US012589366B2

(12) United States Patent
Damren et al.

(10) Patent No.: US 12,589,366 B2
(45) Date of Patent: Mar. 31, 2026

(54) IMPELLER AND SPARGER ASSEMBLIES FOR A BIOPROCESSING SYSTEM

(71) Applicant: Global Life Sciences Solutions USA LLC, Marlborough, MA (US)

(72) Inventors: Richard Damren, Marlborough, MA (US); Timothy Becker, Westborough, MA (US); Colin Tuohey, Marlborough, MA (US); Ralph Stankowski, Marlborough, MA (US); Sree Ramulu Bandaru, Marlborough, MA (US); Saravanan Balakrishnan, Karnataka (IN); Thomas Falkman, Uppsala (SE); Pierre Le Greves, Uppsala (SE); Tomas Dalmo, Uppsala (SE); Nagaraj Rao, Karnataka (IN); Mikael Petersson, Hasselby (SE); Manas Dash, Marlborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 1109 days.

(21) Appl. No.: 17/296,662

(22) PCT Filed: Dec. 4, 2019

(86) PCT No.: PCT/EP2019/083641
§ 371 (c)(1),
(2) Date: May 25, 2021

(87) PCT Pub. No.: WO2020/120251
PCT Pub. Date: Jun. 18, 2020

(65) Prior Publication Data
US 2022/0023807 A1 Jan. 27, 2022

(30) Foreign Application Priority Data

Dec. 14, 2018 (IN) .............................. 201841047368
Dec. 14, 2018 (IN) .............................. 201841047369

(51) Int. Cl.
*C12M 1/00* (2006.01)
*B01F 23/231* (2022.01)
(Continued)

(52) U.S. Cl.
CPC .... *B01F 23/23123* (2022.01); *B01F 23/2311* (2022.01); *B01F 23/233* (2022.01);
(Continued)

(58) Field of Classification Search
CPC ............ B01F 23/23123; B01F 23/2311; B01F 23/233; B01F 27/1111; B01F 33/4535;
(Continued)

(56) References Cited

U.S. PATENT DOCUMENTS 4,288,394 A * 9/1981 Ewing ............... B01F 23/23123
210/220
9,636,644 B2 5/2017 Pradel et al.
(Continued)

FOREIGN PATENT DOCUMENTS

CN 2557520 Y 6/2002
CN 105431224 A 3/2016
(Continued)

OTHER PUBLICATIONS

China National Intellectual Property Administration, Office Action & Search Report for CN Application No. 201980092021.1 dated Feb. 10, 2023 (27 pages including English translation).
(Continued)

*Primary Examiner* — Liban M Hassan
(74) *Attorney, Agent, or Firm* — Eversheds-Sutherland (US) LLP

(57) ABSTRACT

A sparger assembly (700) for a bioprocessing system includes a base plate (710) and at least one aeration manifold (712, 714) removably connected to tire base plate. Each aeration manifold includes at least one inlet for receiving a
(Continued)

gas and a plurality of gas outlet openings for delivering tire gas to a fluid within the bioprocessing system. An impeller assembly (740) fora bioprocessing system includes a hub and at least one blade (742) operatively connected to the hub. The at least one blade includes a first portion connected to the hub and extending generally vertically, and a second portion extending at an upward angle from tire first portion.

17 Claims, 23 Drawing Sheets

(51) Int. Cl.

| | |
|---|---|
| *B01F 23/233* | (2022.01) |
| *B01F 27/1111* | (2022.01) |
| *B01F 33/453* | (2022.01) |
| *B01F 35/513* | (2022.01) |
| *C12M 1/06* | (2006.01) |
| *B01F 101/44* | (2022.01) |

(52) U.S. Cl.
CPC ....... *B01F 27/1111* (2022.01); *B01F 33/4535* (2022.01); *B01F 35/513* (2022.01); *C12M 23/14* (2013.01); *C12M 23/26* (2013.01); *C12M 27/02* (2013.01); *C12M 29/06* (2013.01); *B01F 23/231151* (2022.01); *B01F 23/23125* (2022.01); *B01F 23/231266* (2022.01); *B01F 23/23362* (2022.01); *B01F 2101/44* (2022.01)

(58) Field of Classification Search
CPC ........... B01F 35/513; B01F 23/231151; B01F 23/23125; B01F 23/231266; B01F 23/23362; B01F 2101/44; B01F 27/113; C12M 23/14; C12M 23/26; C12M 27/02; C12M 29/06; C12M 27/04
See application file for complete search history.

(56) References Cited

U.S. PATENT DOCUMENTS

| | | | | |
|---|---|---|---|---|
| 10,618,018 | B2 * | 4/2020 | Kehn | ................... B01J 19/0066 |
| 2004/0174769 | A1 | 9/2004 | Weetman | |
| 2010/0015696 | A1 * | 1/2010 | Claes | .................... B01F 33/813 |
| | | | | 435/303.3 |
| 2012/0275260 | A1 | 11/2012 | Haas et al. | |
| 2012/0313267 | A1 | 12/2012 | Pradel et al. | |
| 2013/0175716 | A1 * | 7/2013 | Weisshaar | ........ B01F 23/23123 |
| | | | | 261/124 |
| 2014/0349385 | A1 | 11/2014 | Erdenberger et al. | |
| 2015/0003189 | A1 | 1/2015 | Werth et al. | |
| 2015/0352003 | A1 | 12/2015 | Walker et al. | |
| 2016/0244710 | A1 | 8/2016 | Wood et al. | |
| 2017/0015573 | A1 | 1/2017 | Neville et al. | |
| 2017/0343005 | A1 | 11/2017 | Kehn | |

FOREIGN PATENT DOCUMENTS

| | | | | |
|---|---|---|---|---|
| DE | 102005010753 | A1 * | 3/2006 | ......... B01F 13/0827 |
| EP | 1776998 | A1 | 4/2007 | |
| EP | 3249237 | A1 | 11/2017 | |
| GB | 223296 | | 10/1924 | |
| IN | 201837007065 | A | 2/2018 | |
| JP | 85759625 | A | 4/1982 | |
| JP | 2004165125 | A | 6/2004 | |
| JP | 2012024727 | A | 2/2012 | |
| JP | 2016190229 | A | 11/2016 | |
| WO | 2012/097079 | A2 | 7/2012 | |
| WO | 2016/158069 | A1 | 10/2016 | |

OTHER PUBLICATIONS

PCT International Search Report and Written Opinion for PCT/EP2019/083641 mailed Jun. 4, 2020 (22 pages).

* cited by examiner

IMPELLER AND SPARGER ASSEMBLIES FOR A BIOPROCESSING SYSTEM

CROSS REFERENCE TO RELATED APPLICATIONS

This application claims the priority benefit of PCT/EP2019/083641, filed on Dec. 4, 2019, which claims the benefit of Indian application Ser. Nos. 20/184,1047368 and 201841047369, which each were filed on Dec. 14, 2018, the entire contents of which are incorporated by reference herein.

BACKGROUND

Technical Field

Embodiments of the invention relate generally to bioprocessing systems and methods and, more particularly, to impeller and sparger assemblies for single-use bioreactor systems.

Discussion of Art

A variety of vessels, devices, components and unit operations are known for carrying out biochemical and/or biological processes and/or manipulating liquids and other products of such processes. In order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

Increasingly, in the biopharmaceutical industry, single use or disposable containers are used. Such containers can be flexible or collapsible plastic bags that are supported by an outer rigid structure such as a stainless steel shell or vessel. Use of sterilized disposable bags eliminates time-consuming step of cleaning of the vessel and reduces the chance of contamination. The bag may be positioned within the rigid vessel and filled with the desired fluid for mixing. An agitator assembly disposed within the bag is used to mix the fluid. Existing agitators are either top-driven (having a shaft that extends downwardly into the bag, on which one or more impellers are mounted) or bottom-driven (having an impeller disposed in the bottom of the bag that is driven by a magnetic drive system or motor positioned outside the bag and/or vessel). Most magnetic agitator systems include a rotating magnetic drive head outside of the bag and a rotating magnetic agitator (also referred to in this context as the "impeller") within the bag. The movement of the magnetic drive head enables torque transfer and thus rotation of the magnetic agitator allowing the agitator to mix a fluid within the vessel. Magnetic coupling of the agitator inside the bag, to a drive system or motor external to the bag and/or bioreactor vessel, can eliminate contamination issues, allow for a completely enclosed system, and prevent leakage. Because there is no need to have a drive shaft penetrate the bioreactor vessel wall to mechanically spin the agitator, magnetically coupled systems can also eliminate the need for having seals between the drive shaft and the vessel.

Depending on the fluid being processed, the bioreactor system may include a number of fluid lines and different sensors, probes and ports coupled with the bag for monitoring, analytics, sampling, and liquid transfer. For example, a harvest port is typically located at the bottom of the disposable bag and the vessel, and allows for a harvest line to be connected to the bag for harvesting and draining of the bag. In addition, existing bioreactor systems typically utilize spargers for introducing a controlled amount of a specific gas or combination of gases into the bioreactor. A sparger outputs small gas bubbles into a liquid in order to agitate and/or dissolve the gas into the liquid. The delivery of gas via spargers helps in mixing a substance, maintaining a homogenous environment throughout the interior of the bag, and is sometimes essential for growing cells in a bioreactor. Ideally, the spargers and the agitator are in close proximity to ensure optimal distribution of the gases throughout the container.

High performance bioreactor systems must provide good bulk mixing in combination with efficient gas dispersion in order to achieve a high gas surface area and bubble size distribution, and thus provide high oxygen transfer rates and kLa (the volumetric mass-transfer coefficient that describes the efficiency with which oxygen can be delivered to a bioreactor for a given set of operating conditions) values desired in intensified cell culture and/or microbial applications. Traditional solutions for achieving high kLa values employ multiple impellers mounted on a single shaft. With single-use bioreactors, however, the use of multiple impellers results in a bulky format of the disposable bag, which cannot be collapsed efficiently. Moreover, longer shafts with multiple impellers requires stabilization, which increases the complexity and cost of the vessel and bag design, and renders bag installation more cumbersome and less user friendly.

In view of the above, there is a need for impeller and/or sparger assemblies that provide for increased oxygen transfer rates and kLa values in a bioreactor system to support increased cell culture cell densities.

BRIEF DESCRIPTION

In a first aspect, a sparger assembly for a bioprocessing system includes a base plate and at least one aeration manifold removably connected to the base. Each aeration manifold includes at least one inlet for receiving a gas and a plurality of gas outlet openings for delivering the gas to a fluid within the bioprocessing system.

In a second aspect, a bioprocessing system includes a vessel, a flexible bioprocessing bag positionable within the vessel, and a sparger assembly positioned at a bottom of the flexible bioprocessing bag. The sparger assembly includes a base plate and at least one aeration manifold removably connected to the base plate. Each aeration manifold includes at least one inlet for receiving a gas and at least one gas outlet opening for delivering the gas to a fluid within the flexible bioprocess bag.

In a third aspect, a sparger assembly for a bioprocessing system includes a base plate, at least one aeration manifold removably connected to the base plate and supported in raised position with respect to the base plate, each aeration manifold including at least one inlet for receiving a gas and at least one gas outlet opening for delivering the gas to a fluid within the bioprocessing system, and a cooperating mounting device enabling coupling of an impeller of the bioprocessing system to the sparger assembly in close association with the aeration manifold.

In a fourth aspect, an impeller assembly for a bioprocessing system includes a hub and at least one blade operatively connected to the hub. The at least one blade includes a first portion connected to the hub and extending generally vertically, and a second portion extending at an upward angle from the first portion.

In a fifth aspect, an impeller assembly for a bioprocessing system includes a hub having a central axis, and a plurality of blades extending from the hub. At least one of the blades is oriented at one of a leading angle or a lagging angle with respect to a radial line extending from the central axis of the hub.

In a sixth aspect, an impeller assembly for a bioprocessing system includes a hub and a plurality of blades extending from the hub, the blades each having a leading edge and a trailing edge. At least one of the blades includes an array of slots or apertures in a leading edge of the blade.

DRAWINGS

The present invention will be better understood from reading the following description of non-limiting embodiments, with reference to the attached drawings, wherein below:

DETAILED DESCRIPTION

Figure 1:
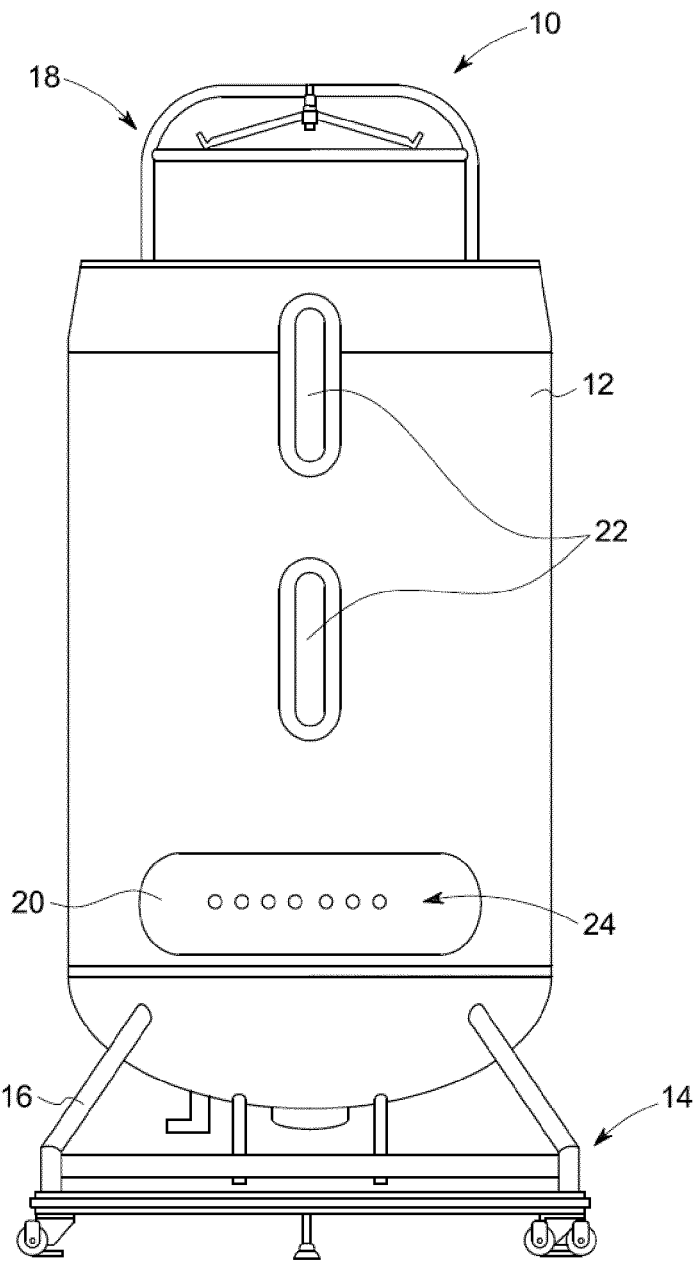
FIG. 1 is a front elevational view of a bioreactor system according to certain embodiments of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as a bioreactor or mixer for the contents within.

As used herein, the term "removably connected" or 'removably coupled" means that the aeration manifolds/sparger elements and base plate are connected in such a way as to be easily connected and/or removed to allow for easy user customization of a sparger assembly without special tools. In other words, "removably connected" is an opposite of "permanently connected".

Embodiments of the invention provide bioreactor systems and sparger assemblies for a bioreactor system. In certain embodiments, a sparger assembly for a bioprocessing system includes a base plate and at least one aeration manifold connected to the base plate in spaced vertical relation to the base plate. Each aeration manifold includes at least one inlet for receiving a gas and a plurality of gas outlet openings for delivering the gas to a fluid within the bioprocessing system.

Embodiments of the invention provide bioreactor systems and impeller assemblies for a bioreactor system. In some embodiments, an impeller assembly for a bioprocessing system includes a hub and at least one blade operatively connected to the hub. The at least one blade includes a first portion connected to the hub and extending generally vertically, and a second portion extending at an upward angle from the first portion.

Figure 2:
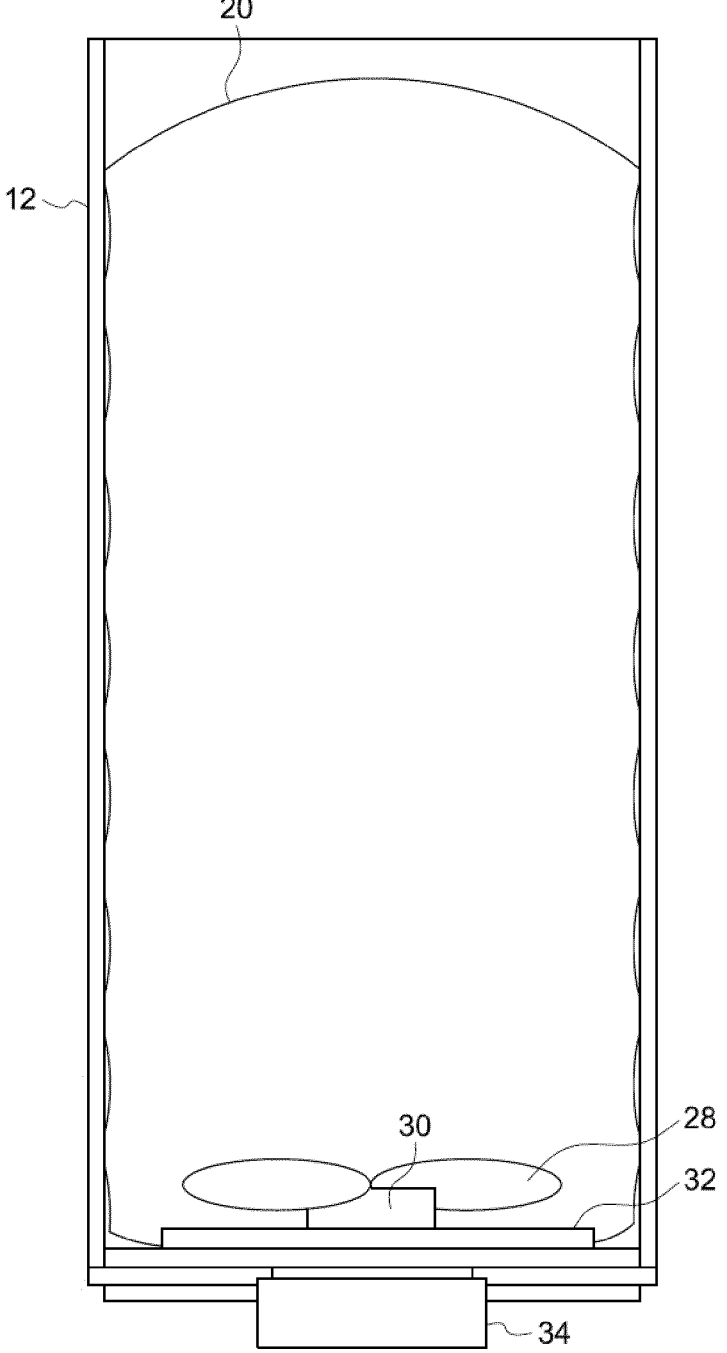
FIG. 2 is a simplified side elevational, cross-sectional view of the bioreactor system of FIG. 1.

With reference to FIGS. 1 and 2, a bioreactor system 10 according to some embodiments of the invention is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift assembly 18 that provides support to a single-use, flexible bag 20 disposed within the vessel 12. The vessel 12 can be any shape or size as long as it is capable of supporting a single-use flexible bioreactor bag 20. For example, according to some embodiments of the invention the vessel 12 is capable of accepting and supporting a 10-2000 L flexible or collapsible bioprocess bag assembly 20.

The vessel 12 may include one or more sight windows 22, which allows one to view a fluid level within the flexible bag 20, as well as a window 24 positioned at a lower area of the vessel 12. The window 24 allows access to the interior of the vessel 12 for insertion and positioning of various sensors and probes (not shown) within the flexible bag 20, and for connecting one or more fluid lines to the flexible bag 20 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide (pCO$_2$), mixing rate, and gas flow rate, for example.

With specific reference to FIG. 2, a schematic side elevational, cutaway view of the bioreactor system 10 is illustrated. As shown therein, the single-use, flexible bag 20 is disposed within the vessel 12 and restrained thereby. In embodiments, the single-use, flexible bag 20 is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra-low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. In some embodiments, the flexible material may be a laminate of several different materials such as, for example Fortem™Bioclear™ 10 and Bioclear 11 laminates, available from GE Healthcare Life Sciences. Portions of the flexible container can comprise a substantially rigid material such as a rigid polymer, for example, high density polyethylene, metal, or glass. The flexible bag may be supplied presterilized, such as using gamma irradiation.

The flexible bag 20 contains an impeller 28 attached to a magnetic hub 30 at the bottom center of the inside of the bag, which rotates on an impeller plate 32 also positioned on the inside bottom of the bag 20. Together, the impeller 28 and hub 30 (and in some embodiments, the impeller plate 32) form an impeller assembly. A magnetic drive 34 external to the vessel 12 provides the motive force for rotating the magnetic hub 30 and impeller 28 to mix the contents of the flexible bag 20. While FIG. 2 illustrates the use of a magnetically-driven impeller, other types of impellers and drive systems are also possible, including top-driven impellers.

In certain embodiments, the impeller plate 32 may be configured as a sparger assembly that is used to introduce a specific gas or air into the fluid within the bag 20 in order to agitate and/or dissolve the air or gas into the fluid. Accordingly, in some embodiments, the impeller and sparger, and the components thereof, form a combined impeller/sparger assembly. In other embodiments, the sparger assembly and the impeller assembly may be separate and/or discrete components. In either implementation, the sparger assembly and the impeller assembly are in close proximity to ensure optimal distribution of gases throughout the bag 20, as discussed in detail hereinafter. As discussed below, it is envisioned that the sparger assembly (which may also serve as an impeller plate supporting the impeller) may take one of various configurations.

Figure 3:
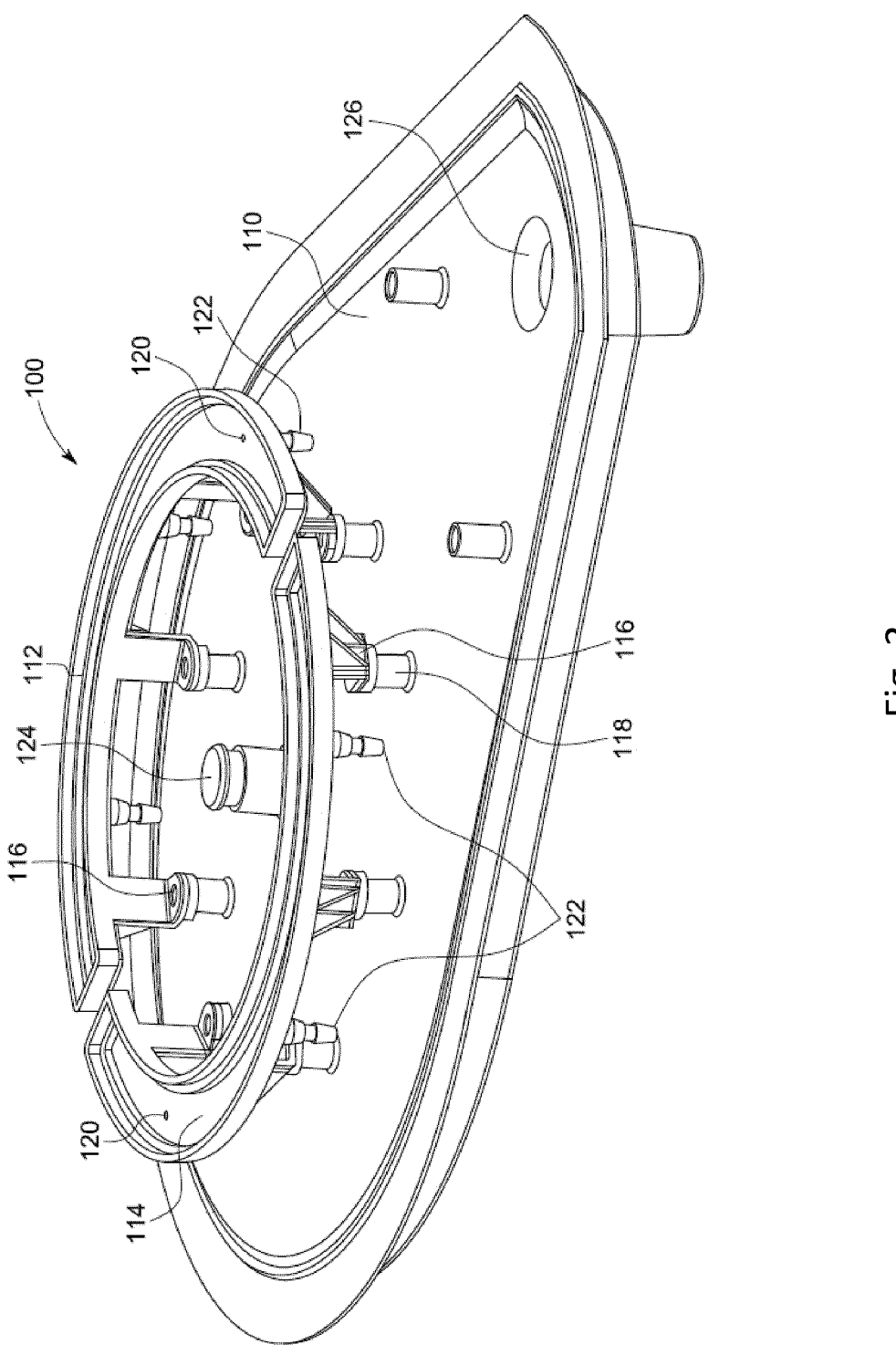
FIG. 3 is a perspective view of a sparger assembly for use with the bioreactor system of FIG. 1, according to certain embodiments of the invention.

For example, FIG. 3 illustrates certain embodiments of a sparger assembly 100 that may be utilized with the flexible bag 20 and bioreactor/bioprocessing system 10. As shown therein, the sparger assembly 100 includes a base plate 110 and a plurality of aeration channels or hollow aeration elements or manifolds 112, 114 connected to the base plate 110. In some embodiments, the aeration manifolds 112, 114 include a plurality of feet 116 that are received on corresponding stand-offs or mounting posts 118 of the base plate 110 such that the aeration manifolds 112, 114 are supported in vertically-spaced relation to (i.e., raised above) the base plate 110. In certain embodiments, the aeration manifolds 112, 114 and base plate 110 may be manufactured as an integral, unitary component. In other embodiments, the aeration manifolds 112, 114 may be manufactured as separate components that may be removably coupled to the base plate 110 through a snap fit, clips, screws or other connection means using the feet 116 and posts 118. As shown in FIG. 3, each of the aeration manifolds 112, 114 may be arc-shaped. In some embodiments, as shown in FIG. 3, the manifolds 112, 114 may be semi-circular arcs and include a plurality of gas outlet openings or apertures 120 in a top surface thereof. In certain embodiments, the gas outlet openings 120 may be pores in a porous frit. The aeration manifolds 112, 114 may also include one or more tube connectors 122 forming an inlet configured for mating connection with a gas supply line (not shown) for delivering gas to the aeration manifolds 112, 114. In some embodiments, the tube connectors 122 are hose barb connectors, although other connector types known in the art may also be utilized without departing from the broader aspects of the invention.

Figure 27:
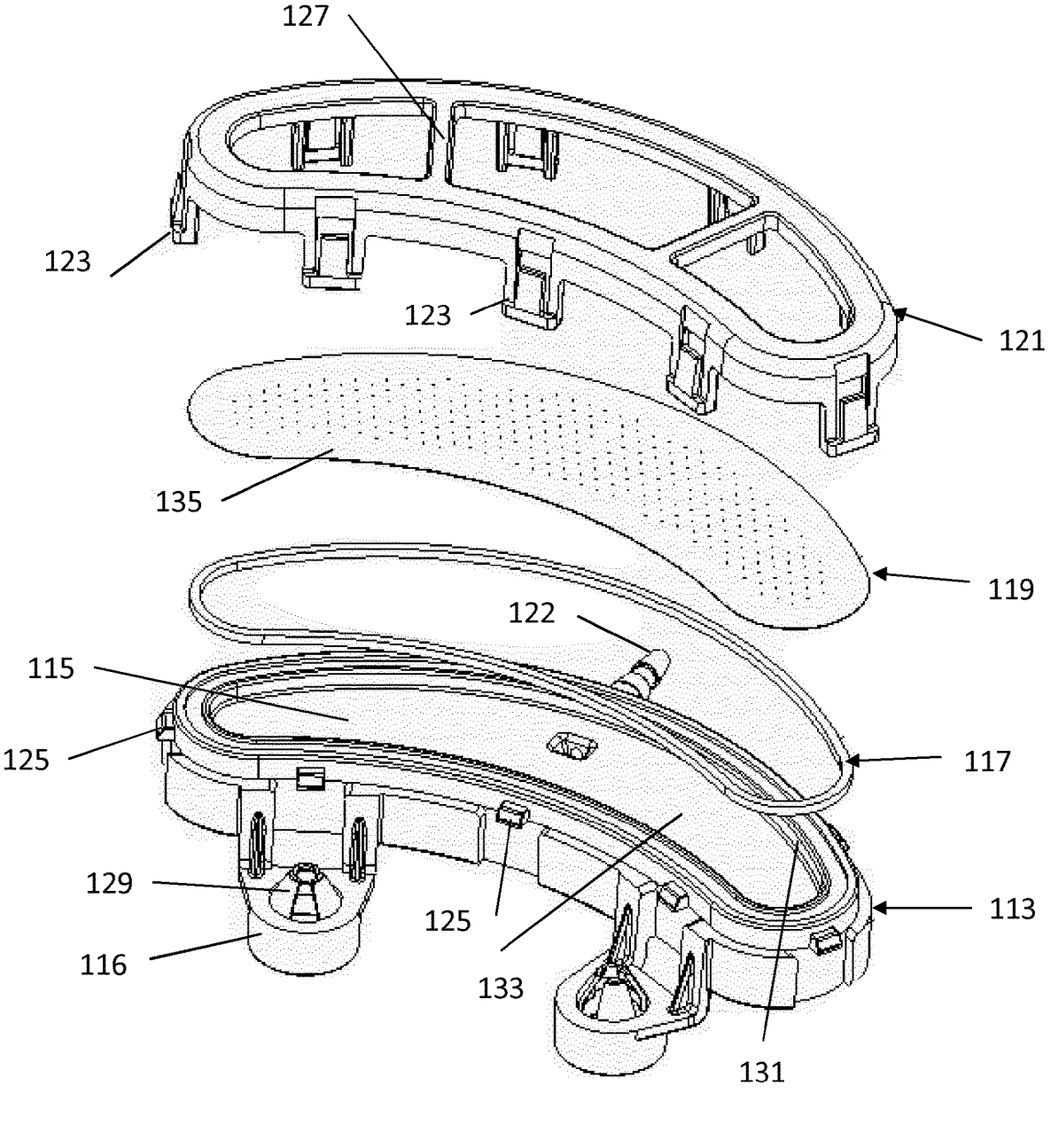
FIG. 27 is an exploded perspective view of a sparger assembly according to certain embodiments of the invention.
Figure 28:
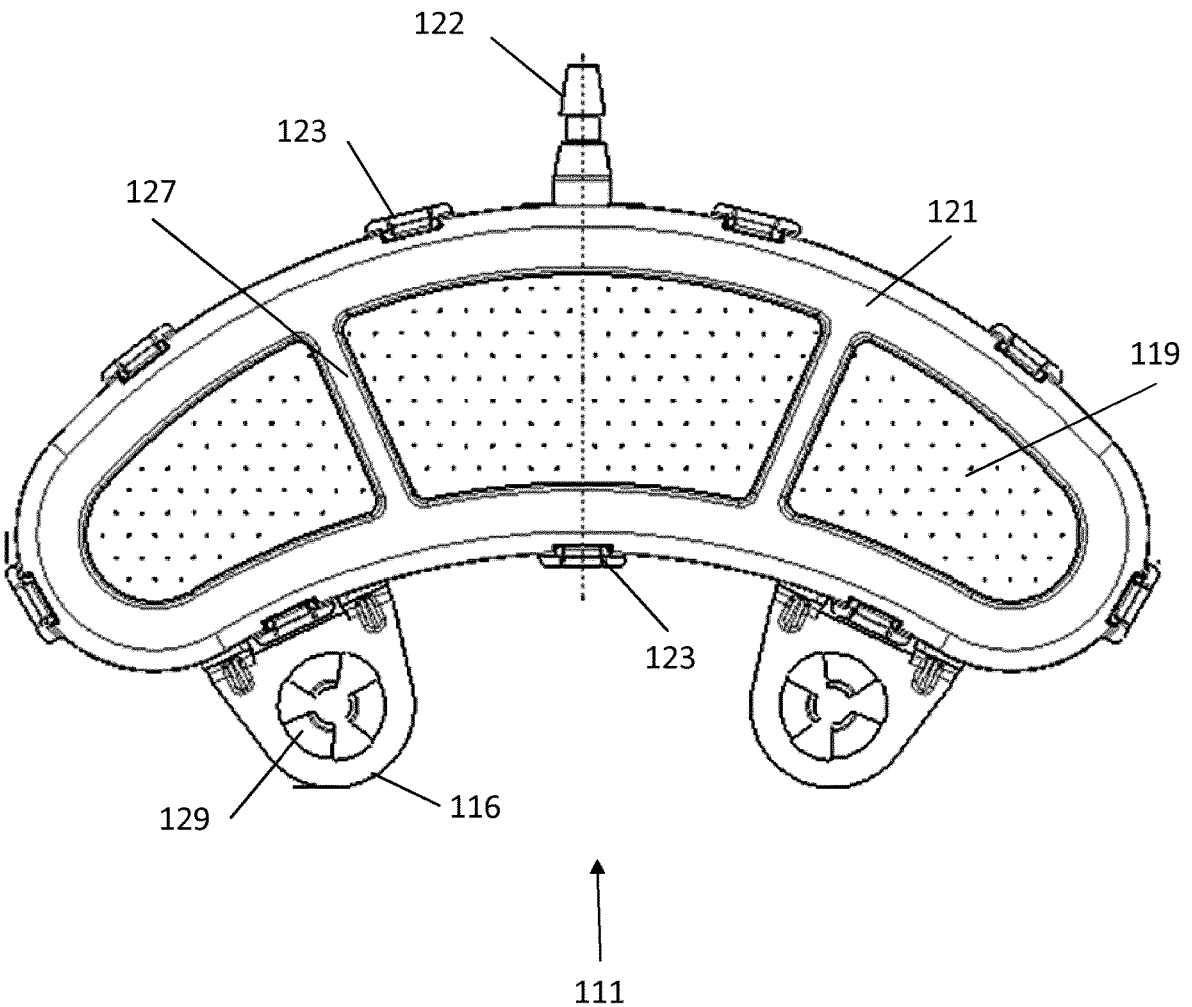
FIG. 28 is a top view of the sparger assembly of FIG. 27.

As illustrated in FIGS. 27 and 28, the aeration manifolds 111 may be assembled from an inlet chamber unit 113 sealed to a porous plate 119 via a gasket 117 and held together by a frame 121. The inlet chamber unit suitably has an inlet chamber 115, delimited by a side wall 131 and a bottom wall 133, in fluidic connection with a tube connector 122 for supply of gas, which is evenly distributed through the inlet chamber to the porous plate. The inlet chamber unit can be mounted on the base plate, e.g. via feet 116 equipped with snap fit elements for forming snap joints with posts on the base plate. The porous plate can then be sealed to the inlet chamber via gasket 117 which is in sealing abutment with side wall 129 and a peripheral portion 135 of the porous plate. Gasket 117 is shown as a separate detail but can also be integrally molded with the side wall 131 of inlet chamber unit 113. The peripheral portion 135 can be non-porous, while the remainder of the plate is porous, either comprising an array of parallel pores or a three-dimensionally connected porous network as in a porous frit. Alternatively, the entire plate is porous. The sealing pressure over the porous plate and gasket can be applied by a frame, connected to the inlet chamber unit e.g. by a plurality of snap joints. The snap joints can e.g. comprise cantilevers 123 extending from the periphery of the frame and engaging lugs or lips 125 in the side wall of the inlet chamber unit. Alternatively, cantilevers extending from the inlet chamber unit may engage lugs/lips in the frame. The frame may further comprise one or more ribs 127 extending across the frame, to prevent pressure bulging of the porous plate.

In certain embodiments, the gas outlet openings 120 may all be the same size. In other embodiments, the gas outlet openings 120 of the first aeration manifold 112 may be a different size than the has outlet openings 120 of the second aeration manifold 114. For example, the gas outlet openings 120 of the first aeration manifold 112 may be smaller than the gas outlet openings 120 of the second aeration manifold 114. In such an implementation, therefore, the first aeration manifold 112, with its comparatively small gas outlet openings 120 that produce relatively small gas bubbles, may be utilized to supply oxygen, while the second aeration manifold 114, with its comparatively large gas outlet openings 120 that produce relatively large gas bubbles, is particularly suited for stripping or sweeping out $CO_2$ with air, for example. Where a porous frit is utilized, the openings/pores will not have the same size, however, the various aeration manifolds may have openings with the same or different average size.

With further reference to FIG. 3, the base plate 110 may include a mounting device enabling coupling of an impeller of the bioprocessing system to the sparger assembly in close association with the aeration manifold. In some embodiments, the mounting device is a vertically-extending mounting shaft 124 centrally located between the two arc-shaped manifolds 112, 114. The shaft 124 is configured to receive the magnetic hub (e.g., hub 30) of an impeller (e.g., impeller 28) and to support the impeller in a position where the lower edge of the impeller blades are positioned just proud of the top surface of the manifolds 112, 114. While embodiments described herein disclose the sparger assembly as having a mounting shaft for receiving an impeller assembly, other cooperating mounting arrangements are possible. For example, the sparger assemblies disclosed herein may have a recessed bearing or receiver structure that is configured to receive a shaft fixed to the impeller. Other coupling arrangements are also possible without departing from the broader aspects of the invention and may include any configuration that employs a retention element to couple the impeller and base plate to one another.

In certain embodiments, the base plate 110 may further include an aperture 126 or fitting for fluid coupling with drain tubing for draining or harvesting of the contents of the flexible bag 20. Incorporating the impeller mounting shaft 124 and the drain aperture 126 into the base plate 110 facilitates positioning of the flexible bag 20 within the bioreactor vessel 12, as well as facilitates alignment of the magnetic hub 30 with the magnetic drive system and drain port in the flexible bag 20 with the drain tubing connected to the bottom of the bioreactor vessel 20.

Figure 4:
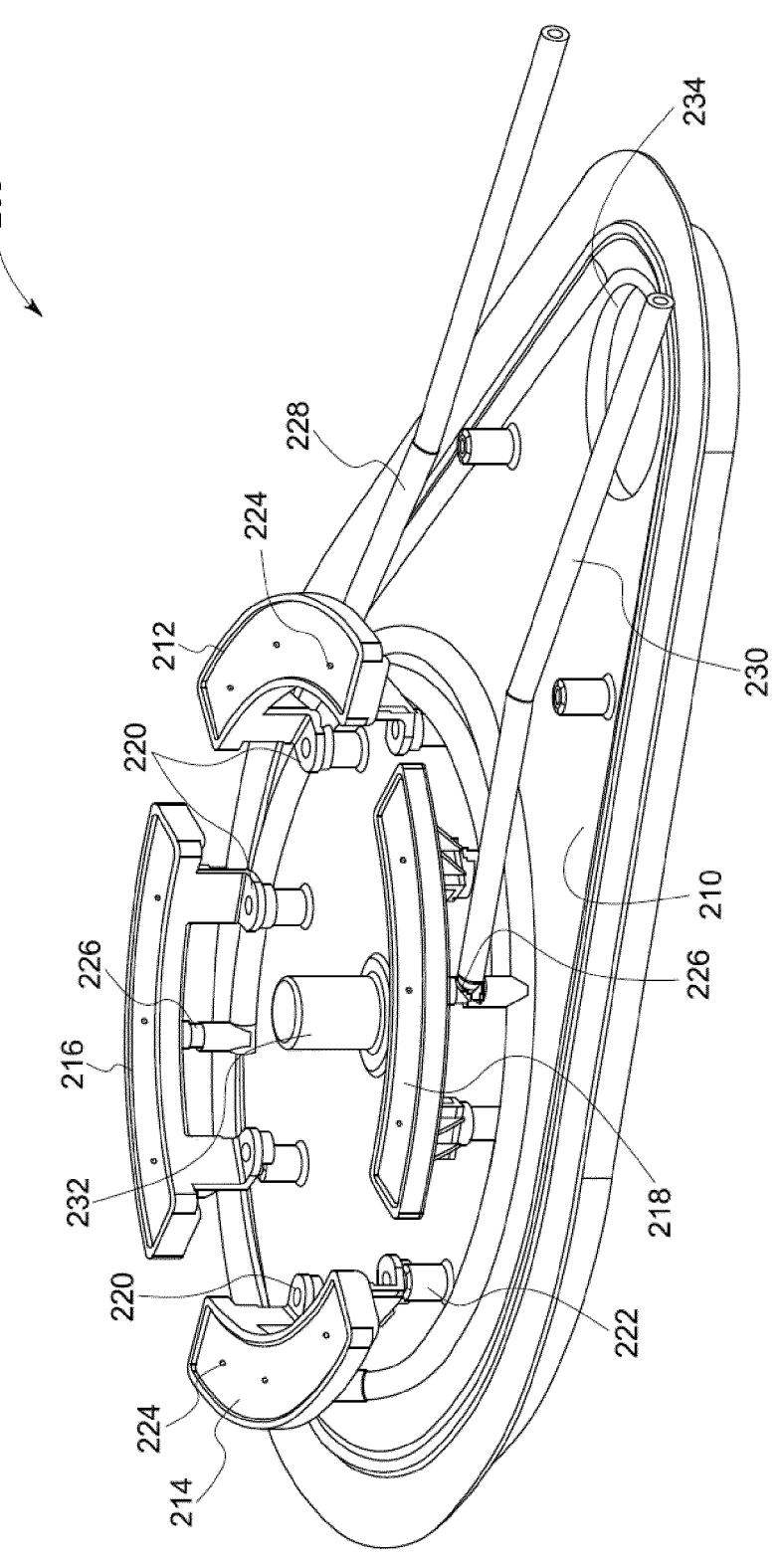
FIG. 4 is a perspective view of a sparger assembly according to certain embodiments of the invention.

Turning now to FIG. 4, a sparger assembly 200 according to some embodiments of the invention is illustrated. As shown therein, the sparger assembly 200 includes a base plate 210 and a plurality of, namely four, aeration channels or hollow aeration manifolds 212, 214, 216, 218 connected to the base plate 210. In some embodiments, the aeration manifolds 212, 214, 216, 218 include a plurality of feet 220 that are received on corresponding stand-offs or mounting posts 222 of the base plate 210 such that the aeration manifolds are supported in vertically-spaced relation to (i.e., raised above) the base plate 210, as described above. As also described above, the aeration manifolds and base plate may be manufactured as an integral, unitary component, or as separate components that may be removably coupled to the base plate 210 through a snap fit, clips, screws or other connection means using the feet 220 and posts 222.

As shown in FIG. 4, each of the aeration manifolds may be quarter-circular arcs and include a plurality of gas outlet openings or apertures 224 in a top surface thereof. The aeration manifolds 212, 214, 216, 218 may also include one or more tube connectors 226 forming an inlet configured for mating connection with one or more gas supply lines, e.g., lines 228, 230 for delivering gas to the aeration manifolds. In certain embodiments, the tube connectors 226 are hose barb connectors, although other connector types known in the art may also be utilized without departing from the broader aspects of the invention.

Similar to the embodiments of FIG. 3, the gas outlet openings 224 of each aeration manifold may be the same size. In other embodiments, the size of the gas outlet openings 224 of at least one of the aeration manifolds may be different from the size of the gas outlet opening s 224 of at least another of the aeration manifolds. For example, in some embodiments, a first pair of opposing aeration manifolds, e.g., aeration manifolds 212, 214 on opposite sides of the circle formed by the arrangement of the manifolds on the base plate 210, may have gas outlet openings 224 of a first size that is different from the size of the gas outlet openings 224 of a second pair of opposing aeration manifolds, e.g., aeration manifolds 216, 218 on opposite sides of the circle formed by the arrangement of the manifolds on the base plate. As disclosed above, the aeration manifolds with the smaller gas outlet openings may be utilized to supply oxygen, while the aeration manifolds with the larger gas outlet openings may be utilized to strip or sweep out $CO_2$, with air, for example.

In certain embodiments, an immediately adjacent pair of aeration manifolds, e.g., aeration manifolds 212, 216 may have gas outlet openings 224 of a first size, while another immediately adjacent pair of aeration manifolds, e.g., aeration manifolds 214, 218 may have gas outlet openings of a second size, wherein the second size is different from the first size. The configuration of the base plate 210 and aeration manifolds 212, 214, 216, 218, and the selectively removable nature of the aeration manifolds, allows the configuration of the sparger assembly 200 to be easily adjusted according to user preferences. In particular, this design allows for plug-and-play like functionality, enabling a user to mount various combinations of aeration manifolds to the base plate 210 to provide a sparger assembly of various configurations. For example, a user can easily mount three aeration manifolds with smaller gas outlet openings 224 in combination with a single aeration manifold with larger gas outlet openings 224 to increase oxygen delivery to the system, where desired, or mount three aeration manifolds with larger gas outlet openings 224 in combination with a single aeration manifold with smaller gas outlet openings 224 to enhance $CO_2$ removal, without having to adjust rate of gas delivery to the sparger assembly 200.

As discussed above in connection with FIG. 3, the base plate 210 may include a vertically-extending mounting shaft 232 centrally located between the aeration manifolds for receiving an impeller assembly. Moreover, as discussed above, the base plate 210 may include an aperture 234 or fitting for fluid coupling with drain tubing for draining or harvesting of the contents of the flexible bag 20.

Figure 5:
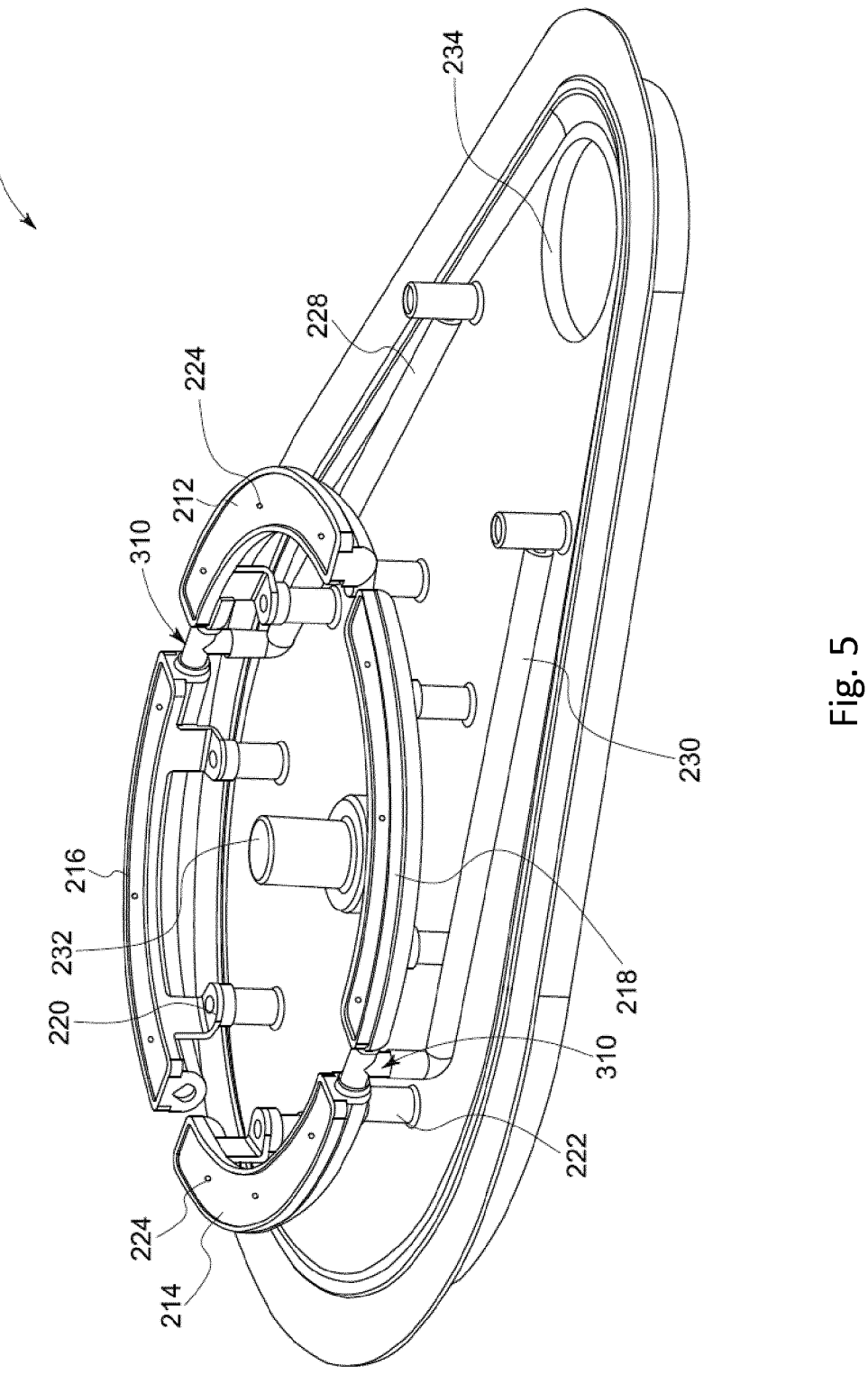
FIG. 5 is a perspective view of a sparger assembly according to certain embodiments of the invention.

Referring now to FIG. 5, a sparger assembly 300 according to some embodiments of the invention is illustrated. The sparger assembly 300 is similar in configuration to the sparger assembly 200 of FIG. 4, where like reference numerals designating like parts. Rather than each aeration manifold having a hose barb connector for connection with a gas supply line, however, a T-fitting 310 is utilized to fluidly interconnect two adjacent aeration manifolds (e.g., aeration manifold 212 and aeration manifold 216, and aeration manifold 214 and aeration manifold 218), as well as connect the gas supply lines 228, 230, respectively, to the aeration manifolds. In one implementation, the fluidly interconnected aeration manifolds may each have gas outlet openings 224 of the same size. In another implementation, the first pair of interconnected aeration manifolds (e.g., aeration manifolds 212, 216) may have gas outlet openings 224 of a size that is different from a size of the gas outlet openings 224 of the second pair of interconnected aeration manifolds (e.g., aeration manifolds 214, 218). In yet another implementation, all of the manifolds may have gas outlet openings 224 of the same size.

Figure 6:
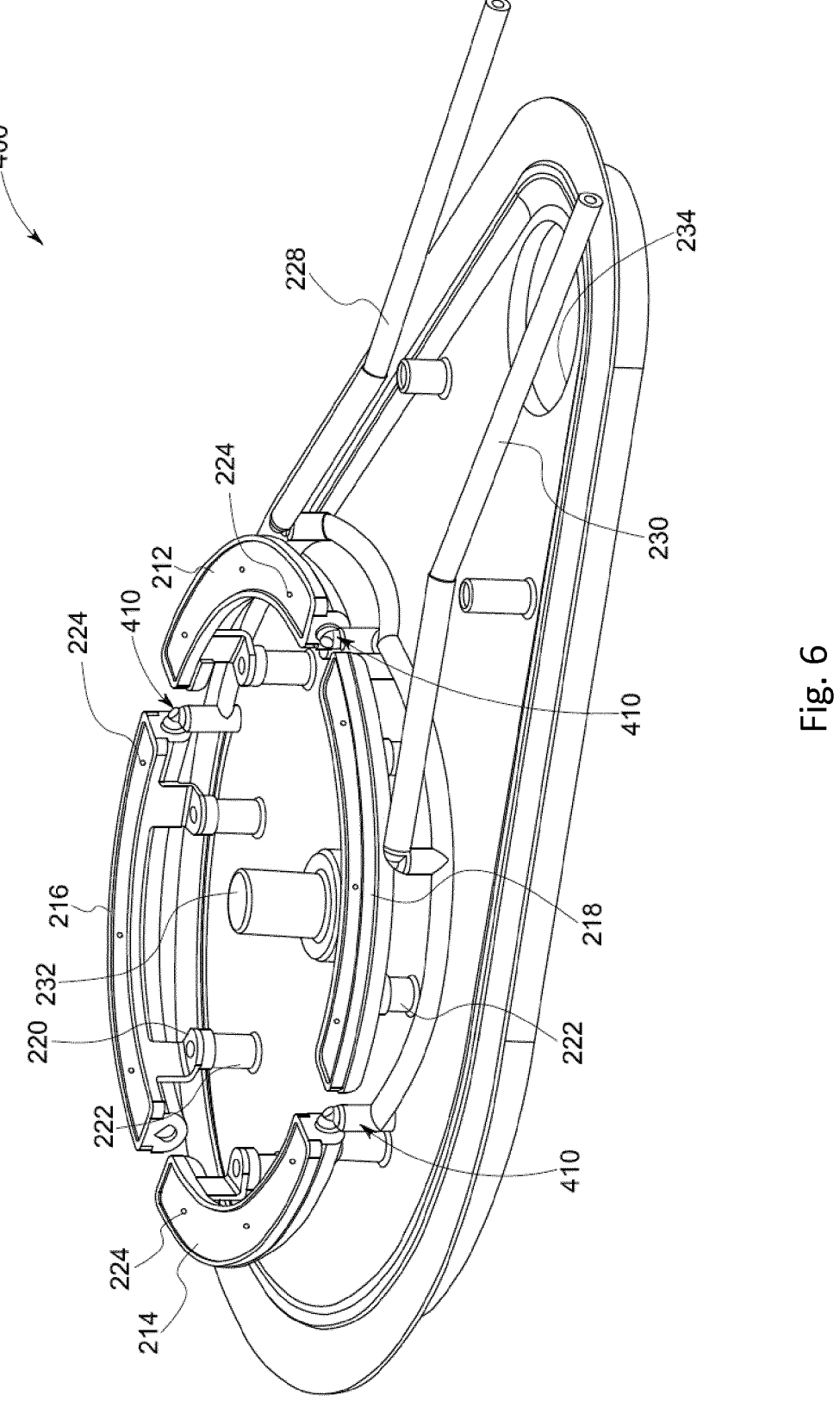
FIG. 6 is a perspective view of a sparger assembly according to certain embodiments of the invention.

With reference to FIG. 6, a sparger assembly 400 according to certain embodiments of the invention is illustrated. The sparger assembly 400, is similar in configuration to the sparger assembly 200 of FIG. 4, where like reference numerals designating like parts. Rather than each aeration manifold having a hose barb connector for connection with a gas supply line, however, an elbow fitting 410 is utilized to connect the gas supply lines 228, 230, respectively, to the aeration manifolds 212, 214, 216, 218. For example, elbow fittings 410 may be utilized to connect a first gas supply line 228 to the aeration manifolds 212, 216, as well as connect a second gas supply line 230 to the aeration manifolds 214, 218. As described above, some of the aeration manifolds may be configured with gas outlet openings 224 that have a different size than those of other aeration manifolds. In some embodiments, the aeration manifolds that are connected to a common supply line may have the same size gas outlet openings 224.

While FIGS. 3-6 illustrate sparger assemblies having two or four discrete aeration manifolds, it is contemplated that base plate may be manufactured with support posts 222 that are configured to receive three, or more than four, aeration manifolds of any partial-circle shape (i.e., any segment of a circle). In particular, the sparger assembly may include any number of arc-shaped aeration manifolds that together form a broken (or unbroken) circular arc. In certain embodiments, the individual arc components may be isolated components in a generally circular or annular arc, which may be manufactured through additive manufacturing technologies. The base plate therefore allows the sparger assembly to be easily configured according to user preferences, and easily adapted to the particular bioprocess being carried out in the bioreactor system 210. As discussed above, the aeration manifolds may be configured for removable connection to the base plate to allow for easy customization of the sparger assembly.

Figure 7:
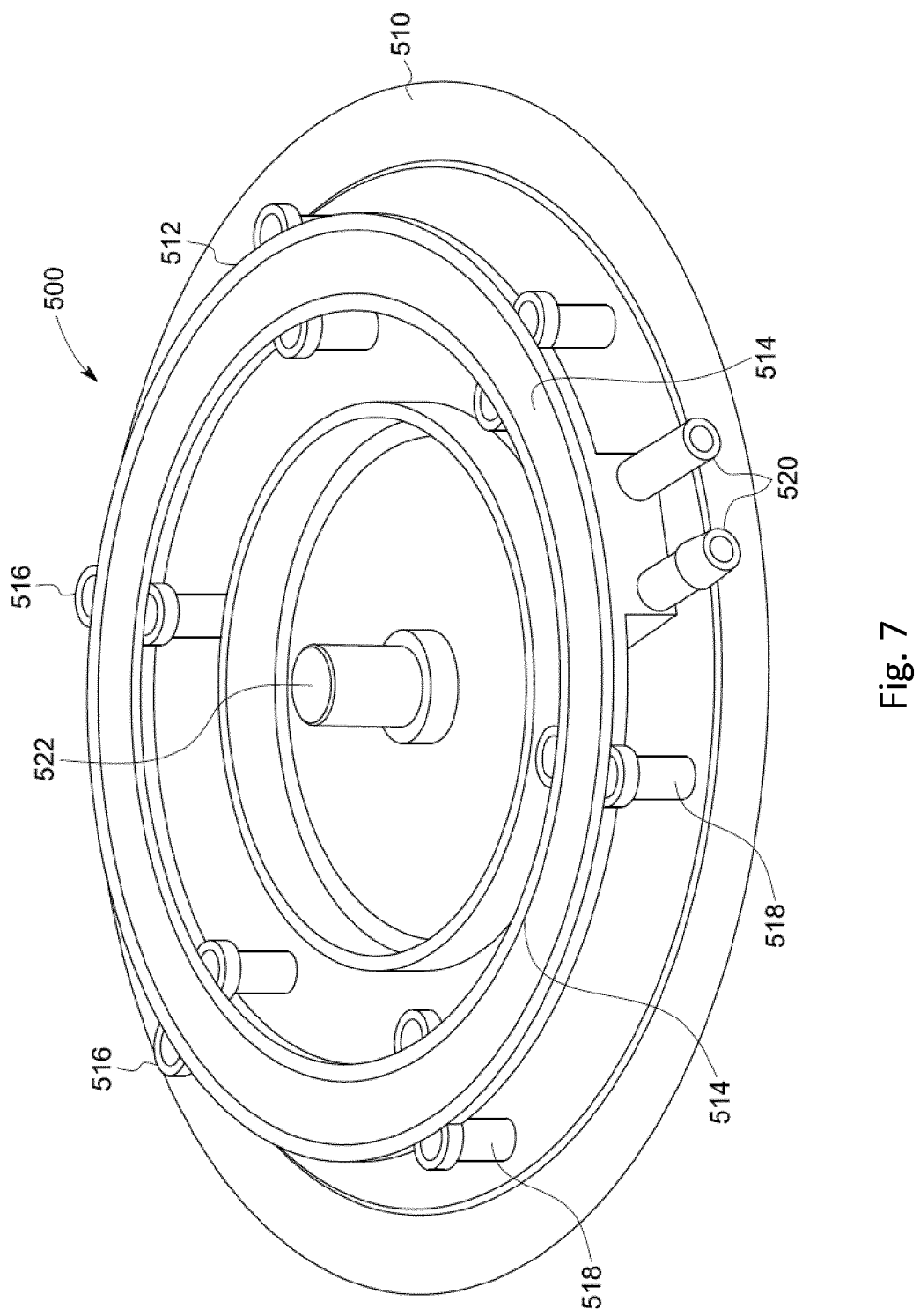
FIG. 7 is a perspective view of a sparger assembly according to certain embodiments of the invention.

Turning now to FIG. 7, a sparger assembly 500 according to some embodiments of the invention is illustrated. As shown therein, the sparger assembly 500 includes a generally circular base plate 510 and an annular aeration manifold 512 removably connected to base plate 510. Similar to the embodiments discussed above, the aeration manifold 512 includes a plurality of gas outlet openings 514 and is raised above the base plate 510. In some embodiments, the aeration manifold 512 may include a plurality of feet 516 that are received by stand-offs or posts 518 of the base plate 510 to support the manifold 510 in vertically-spaced relation to the base plate. The aeration manifold 512 may also include one or more tubing connectors 520 for connecting one or more gas supply lines to the aeration manifold 512, in the manner described above. Similar to the embodiments described above, the base plate 510 may include a vertically-extending mounting shaft 522 located in the center of the aeration manifold 512 for receiving an impeller assembly.

Figure 8:
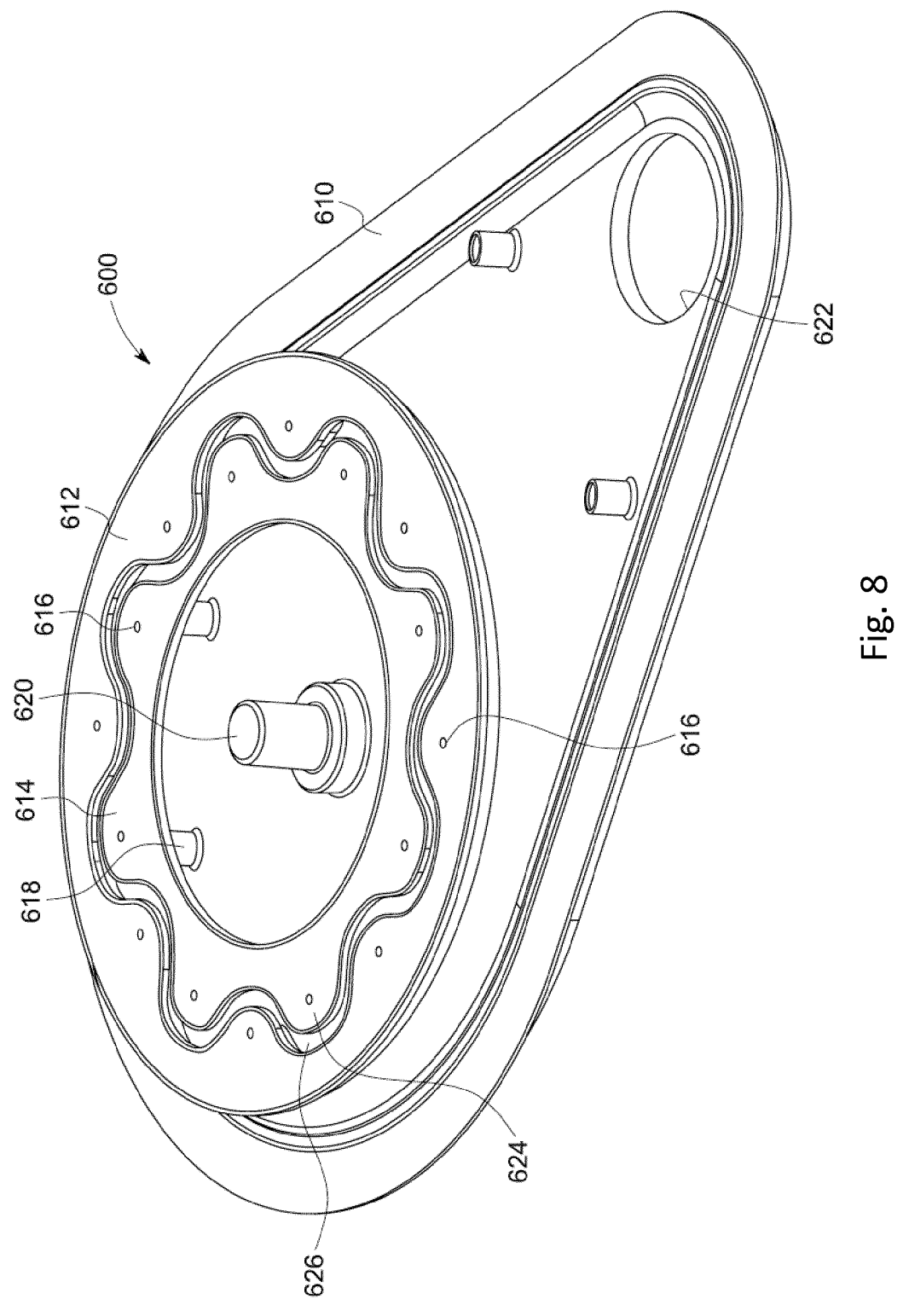
FIG. 8 is a perspective view of a sparger assembly according to certain embodiments of the invention.

With reference to FIG. 8, a sparger assembly 600 according to certain embodiments of the invention is shown. The sparger assembly 600 includes base plate 610 and a pair of nested aeration manifolds 612, 614 connected to base plate 610. Similar to the embodiments discussed above, each aeration manifold 612, 614 includes a plurality of gas outlet openings 616 and is raised above the base plate 610 (e.g., supported on projecting posts 618 that extend upwardly from the base plate 610. In certain embodiments, the aeration manifolds 612, 614 are removably coupled to the base plate 610 and include tubing connectors (not shown) for connecting one or more gas supply lines (not shown) to the aeration manifolds 612, 614, in the manner described above. Similar to the embodiments described above, the base plate 610 may include a vertically-extending mounting shaft 620 located in the center of the aeration manifolds 612, 614 for receiving an impeller assembly of the bioreactor system 10. Moreover, the base plate 610 may include an aperture 622 or fitting for fluid coupling with drain tubing for draining or harvesting of the contents of the flexible bag 20.

As shown in FIG. 8, the aeration manifolds 612, 614 may have a pleated or sprocket shape. In particular, in some embodiments, the outer aeration manifold 612 may have an inner periphery that is generally sprocket shaped, and the inner aeration manifold 614 may have an outer periphery that is likewise generally sprocket shaped. The inner aeration manifold 614 may be sized and oriented so that the 'teeth' or peaks 624 of the inner aeration manifold 614 are received in corresponding recesses or grooves 626 in the outer aeration manifold 612. In some embodiments, the gas outlet openings 616 of the aeration manifolds 612, 614 may be the same or a different size.

Figure 9:
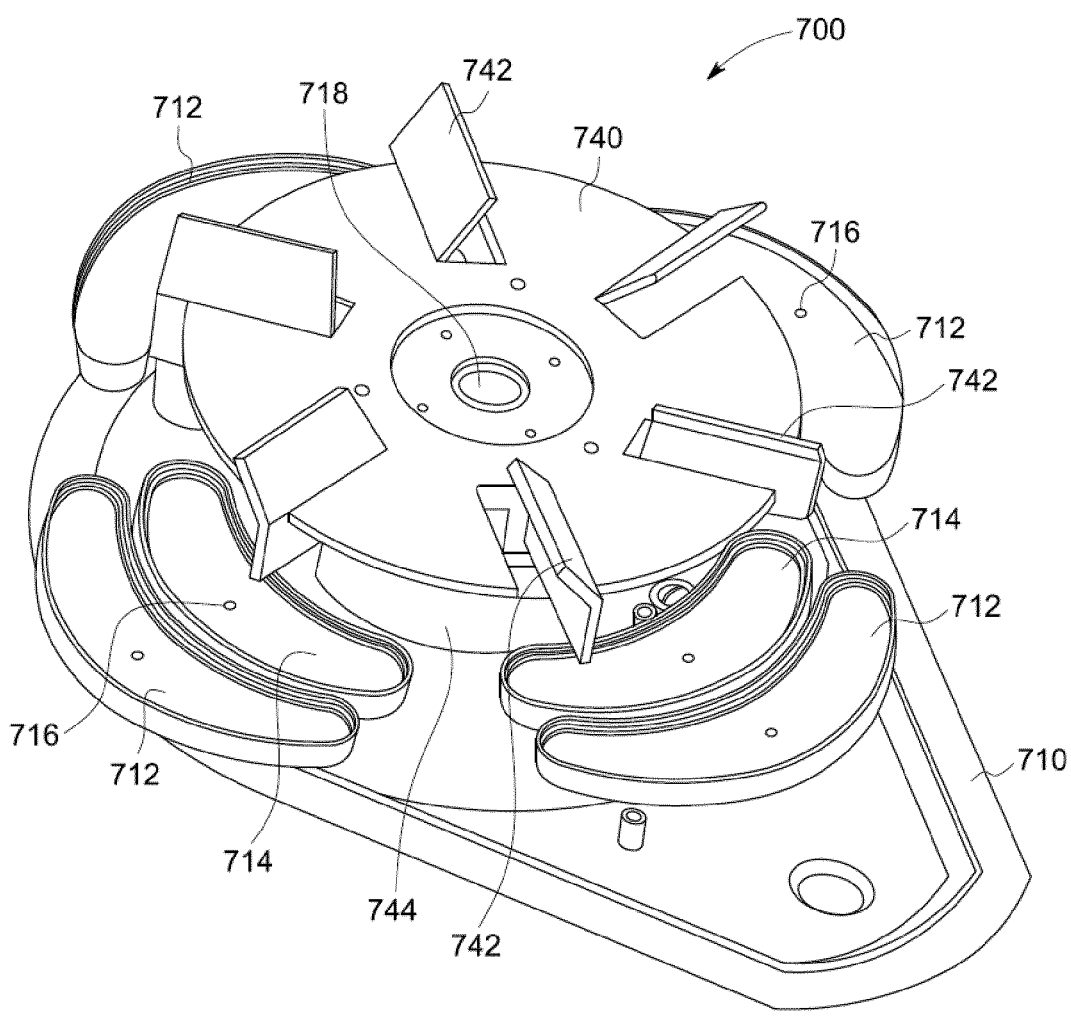
FIG. 9 is a perspective view of a sparger assembly according to certain embodiments of the invention, shown with an impeller assembly mounted thereon.
Figure 10:
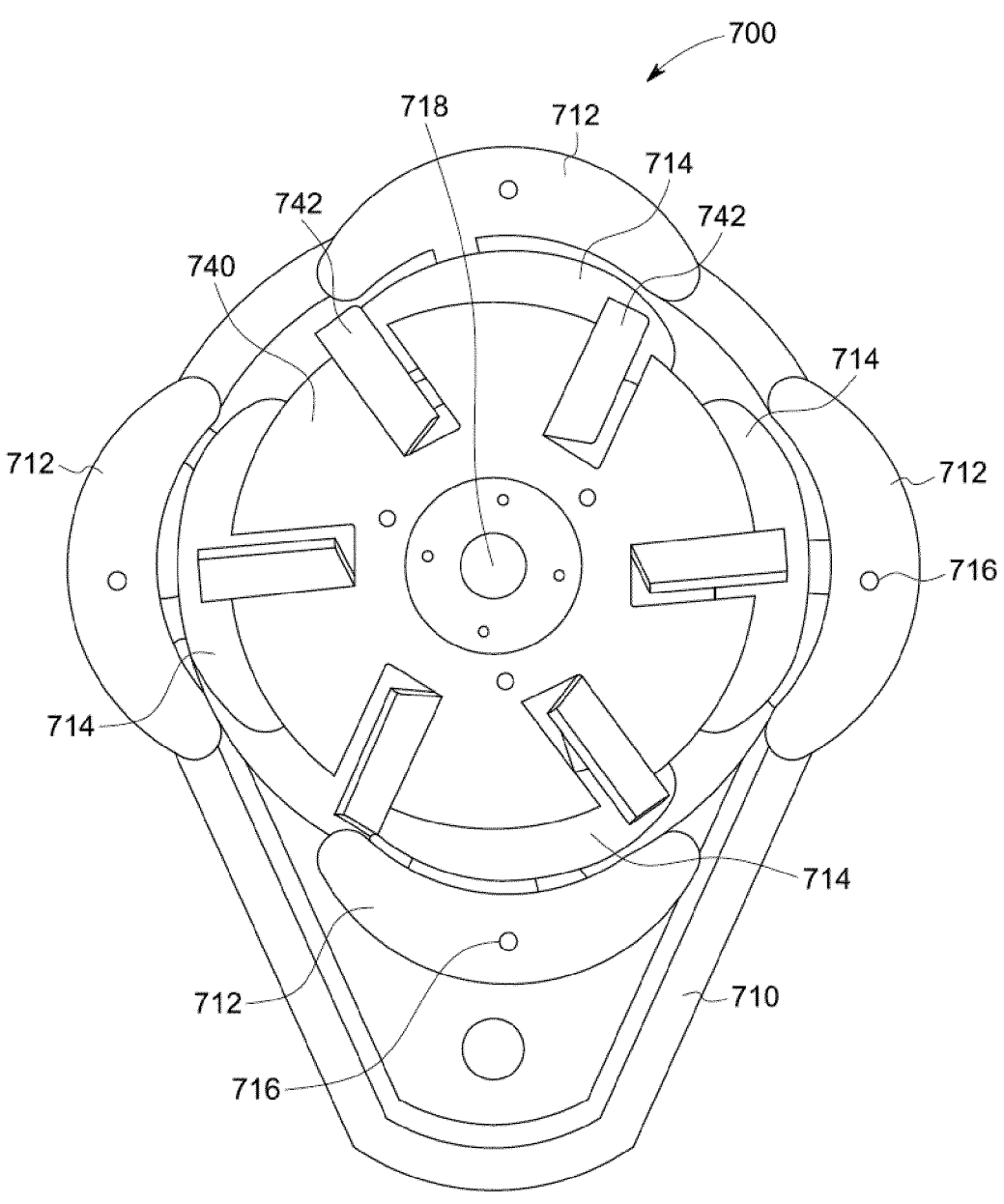
FIG. 10 is a top plan view of the sparger assembly of FIG. 9.
Figure 11:
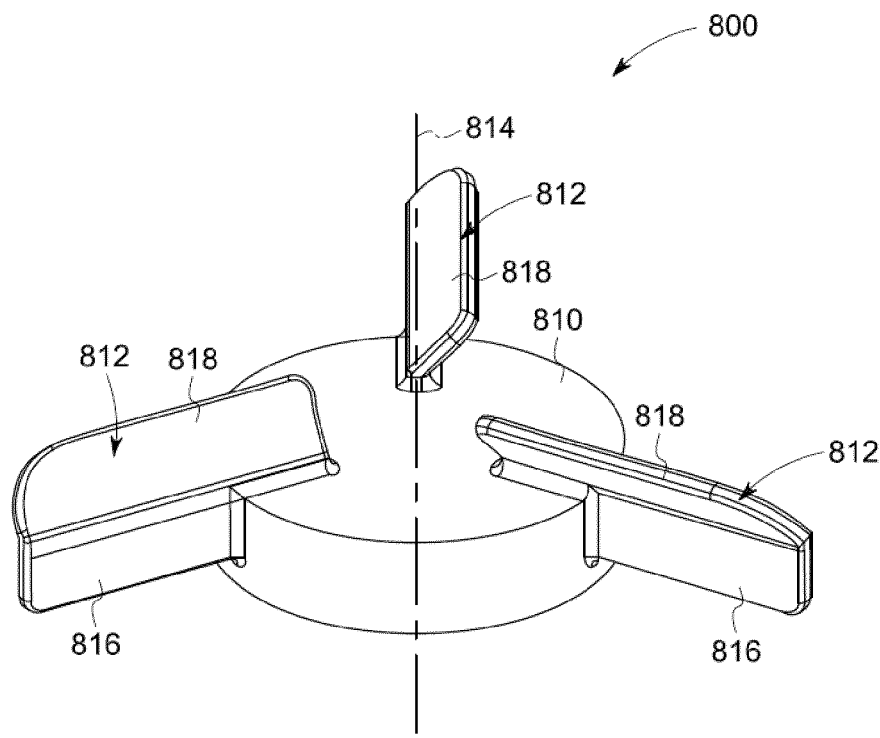
FIG. 11 is a perspective view of an impeller assembly for use with the bioreactor system of FIG. 1, according to certain embodiments of the invention.
Figure 12:
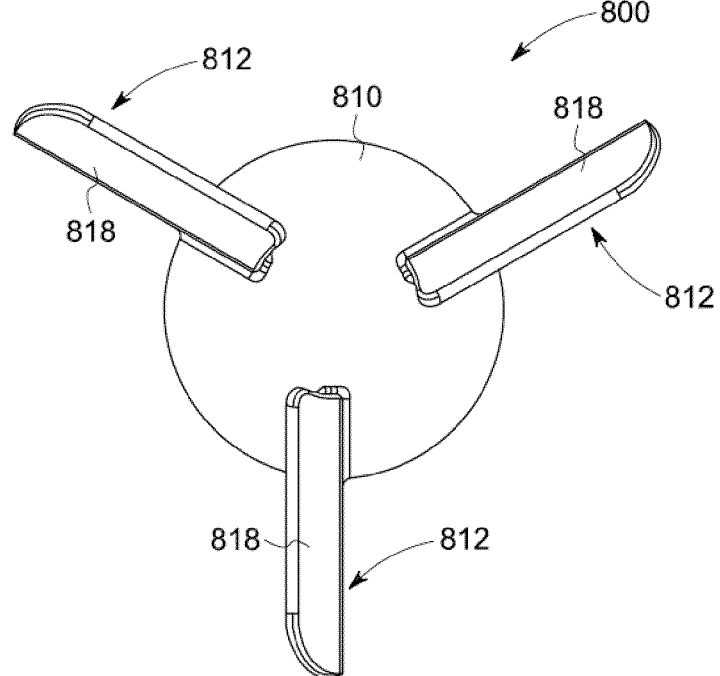
FIG. 12 is a top plan view of the impeller assembly of FIG. 11.

FIGS. 9 and 10 illustrate certain embodiments of a sparger assembly 700 having a base plate 710 and plurality of aeration manifolds supported on the base plate in raised or spaced vertical relationship to the base plate 710, according to some embodiments of the invention. As shown therein, the aeration manifolds may include a plurality of outer, arch-shaped aeration manifolds 712 and a plurality of inner, arch-shaped manifolds 714 nested with, or positioned at a radial location inward of, the outer aeration manifolds 712. The aeration manifolds 712, 714 each include at least one gas outlet opening 716, the function of which has been hereinbefore described. The aeration manifolds 712, 716 are supported in a raised position above the base plate 710 by a plurality of posts or projections (not shown), as likewise hereinbefore described.

In certain embodiments, the inner aeration manifolds 714 and outer aeration manifolds are raised above the support plate 710 at substantially the same distance (e.g. with less than 5%, such as less than 1%, difference in the distance to the support plate). In certain embodiments, as best shown in FIG. 9, the inner aeration manifolds 714 are positioned closer to the top surface of the base plate 710 than are the outer aeration manifolds 712. In this respect, the outer aeration manifolds are raised above the base plate 710 to a greater extent than the inner aeration manifolds. This configuration allows the inner aeration manifolds 714 to be positioned beneath the blades of an impeller assembly 740 received on the impeller support shaft 718 (via a hub 744), and allows gas from the inner aeration manifolds 714 to be released through the gas outlet openings 716 thereof beneath the blades 742 of the impeller assembly 740. As shown in FIG. 10, gas from the outer aeration manifolds 712 may be released through the gas outlet openings 716 thereof at a radial location outward of the blades 742 of the impeller assembly 740, due to the positioning of the outer aeration manifolds 712 radially outward of the impeller blades.

Figure 22:
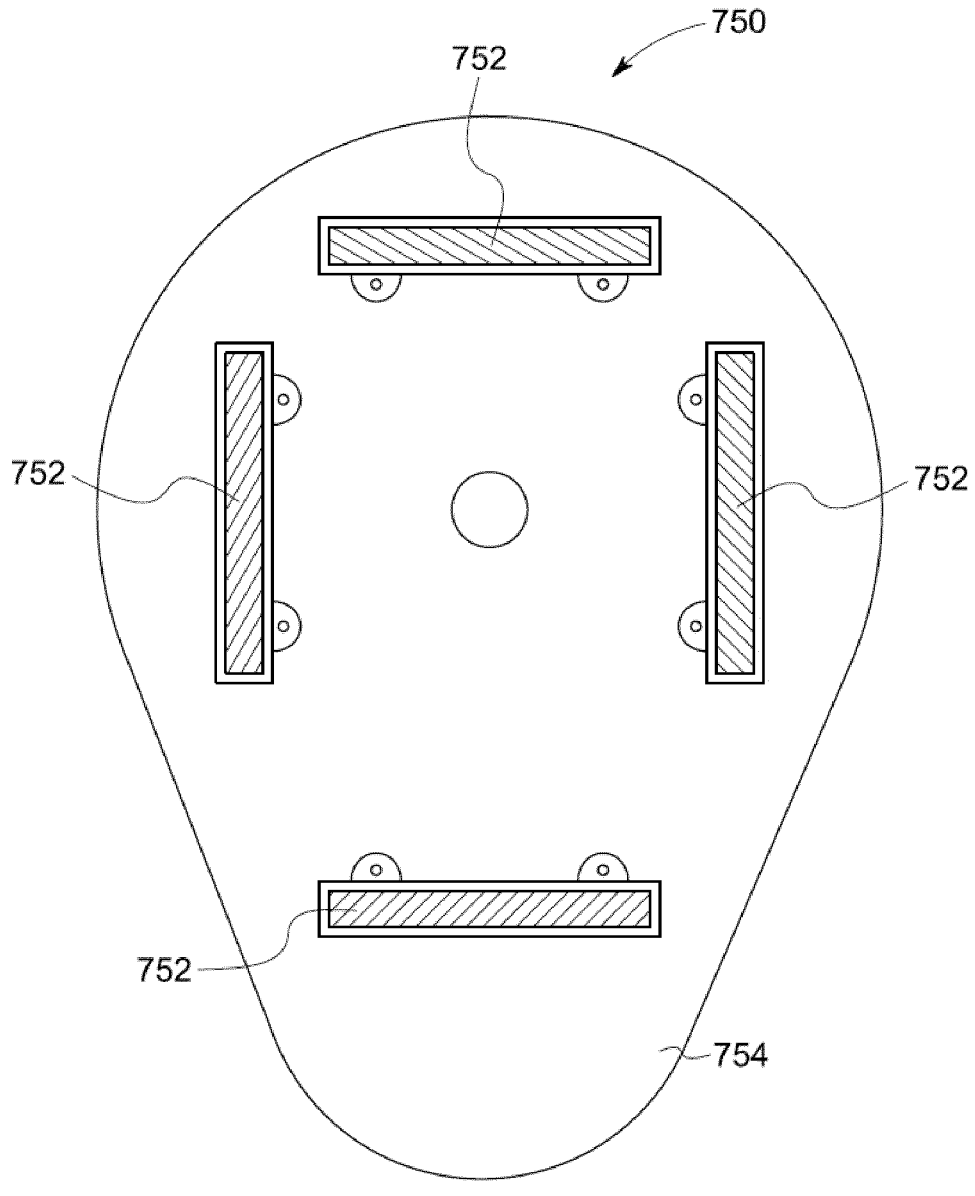
FIG. 22 is a top plan view of one arrangement of aeration manifolds of a sparger assembly, according to certain embodiments of the invention.

While the sparger assemblies of the invention have hereinbefore been described as having sparger elements/aeration manifolds that are arc or arch shaped, and arranged in a manner so as to form a circle or portion of an arc, the invention is not so limited in this regard. In particular, the aeration manifolds, themselves, may have any shape desired (e.g., rectangular, triangular, ovular, etc.) and may be arranged in an annular, circular, rectangular or any polygon shape. Other arrangements of the aeration manifolds on the base plate are also possible. For example, FIG. 22 illustrates a sparger assembly 750 having aeration manifolds 752 that are generally rectangular in shape, and which are removably mounted to the base plate 754 to form a generally rectangular array. In any embodiment, each aeration manifold may be separately or individually connected to a supply of a gas or gasses so that multiple gases can be delivered to each aeration manifold segment, as desired.

Figure 23:
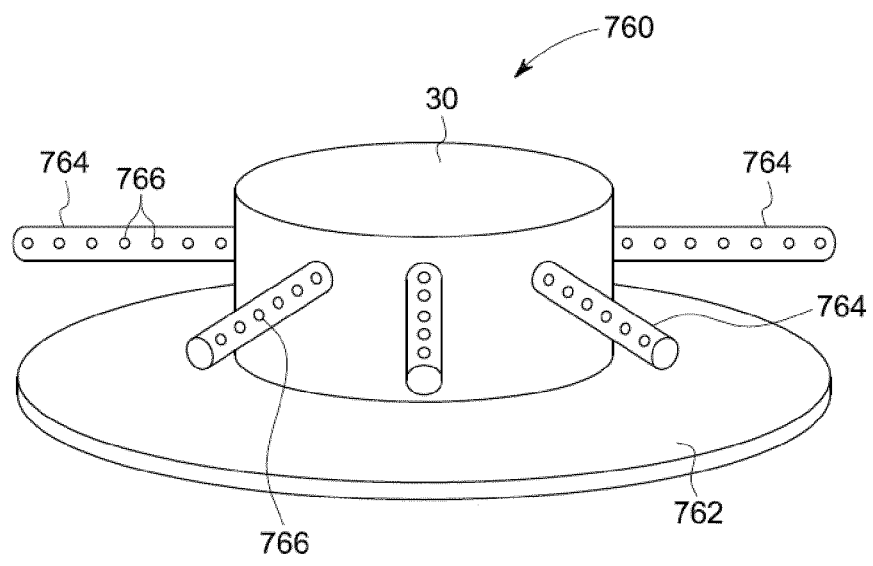
FIG. 23 is a perspective view of a sparger assembly according to certain embodiments of the invention.
Figure 24:
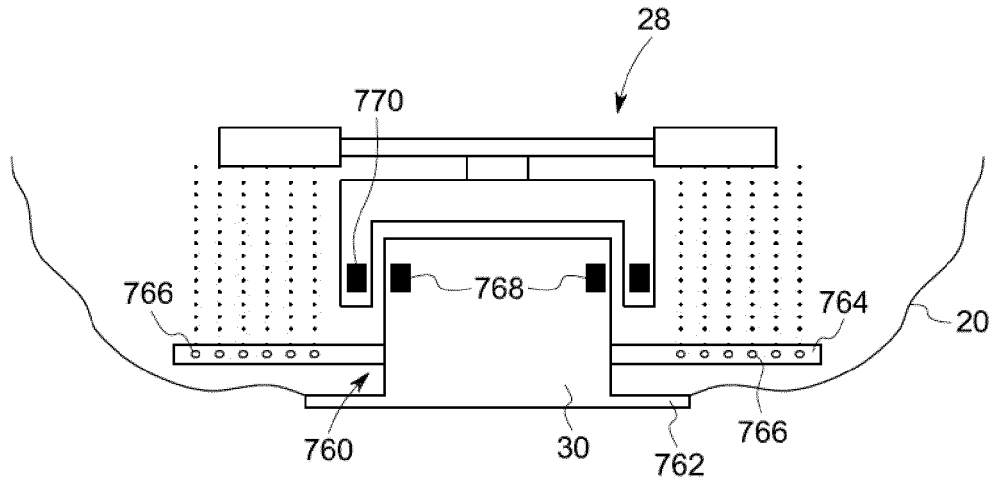
FIG. 24 is a side elevational view of the sparger assembly of FIG. 23, shown in use in a flexible bioreactor bag.

Turning to FIGS. 23 and 24, a sparger assembly 760 according to some embodiments of the invention is shown. Rather than having aeration manifolds that are mounted in vertically-spaced relation to the base plate, however, the sparger assembly 760 includes a base plate 762 having a hub (e.g., magnetic hub 30), and sparger elements or aeration manifolds 764 that extend radially from the hub 30. While not mounted to the planar portion of the base plate 762, the aeration manifolds are vertically spaced from the base plate. The aeration manifolds 764 have gas outlet openings 766, holes or pores that allow for the dispersion of gas into the interior of the flexible bioreactor bag 20, as described above. The aeration manifolds 764 may be removably coupled to the hub 30, although in some embodiments the aeration manifolds 764 may be permanently affixed to the hub 30. As shown in FIG. 24, and as discussed above, the magnetic hub 30 may include magnets 768 that cooperate with magnets 770 of the impeller 28 to rotationally drive the impeller 28.

In connection with the embodiments described above, by providing a sparger assembly that includes aeration manifolds for gas distribution that are raised from the base plate (or at least above a bottom surface of the vessel), sparge gas can be input into the bioreactor in close association with the impeller, which provides for more efficient gas dispersion in order to achieve a high gas surface area and bubble size distribution. Moreover, because the aeration manifolds are removably connected to the base plate, the sparger assembly may be universally configurable and adaptable to provide almost any gas distribution profile desired. In particular, the modular nature of the sparger assemblies described herein (i.e., base plate and removable aeration manifolds) allows for easy customization and creation of a sparger assembly, including customization of gas outlet height, gas outlet opening location, sparging 'density', etc.

In any of the embodiments described above, the interior of the aeration manifolds may be designed for optimized flow distribution such as, for example, by using a manifold groove system that promotes reduced pressure losses. In some embodiments, various components of the sparger assemblies, including the aeration manifolds, may be manufactured through additive manufacturing, which can be used to provide transitions from solid to porous materials with incorporated fluid channels to reduce the number of parts and ease of assembly. While the embodiments described above disclose hollow aeration manifolds having gas outlet openings, the manifolds may also be comprised of a porous frit wherein the openings for gas release are the pores in the porous frit.

In some embodiments, the pattern of apertures, holes or pores in the aeration manifolds of the spargers described herein can be any regular geometric pattern or a random pattern. In certain embodiments, the apertures of one or more of the aeration manifolds may be arranged in a pattern which is configured such that the spacing between the apertures, holes or pores, s, is greater than the diameter of the gas bubbles that are produced by an aperture, hole or pore of diameter, d. Having a spacing between the apertures, holes or pores which is greater than the gas bubbles diameter assists in preventing adjacent gas bubbles from coalescing, as it keeps the bubbles from contacting each other at the surface of the sparger element/aeration manifold. The diameter of a gas bubble produced by an aperture, hole or pore of a specific diameter is dependent not only on the diameter of the hole or pore but is also greatly affected by factors such as the surface energy of the material from which the sparger is constructed and also on the physical and chemical properties of the liquid in which the bubbles are being created since that affects the surface tension of the air/liquid interface of the gas bubble surface.

Figure 21:
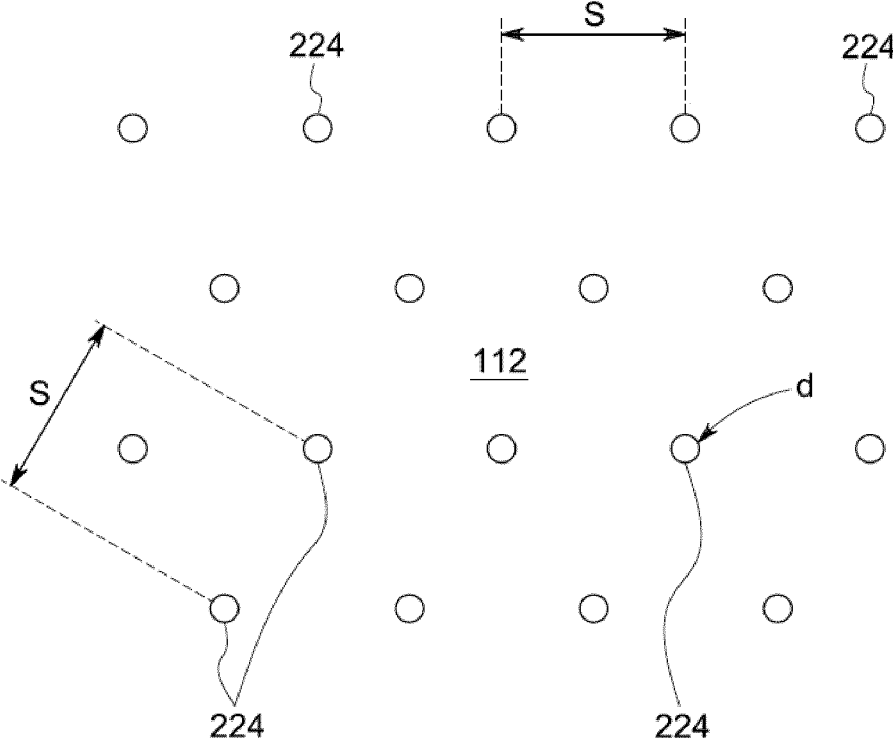
FIG. 21 is a schematic illustration of an arrangement of apertures in a sparger element/aeration manifold, according to certain embodiments of the invention.

With reference to FIG. 21, an example of a geometric pattern for the location of the openings, holes or pores in the surface of an aeration manifold is shown. As illustrated in FIG. 21, the number of holes (e.g., holes 224) in the sparger element/aeration manifold (e.g., aeration manifold 112) is maximized by arranging the holes in a pattern of equilateral triangles, where the holes are located at the apexes of the triangles. This pattern is sometimes also referred to as a hexagonal pattern. This pattern maximizes the number of holes that could be created in a sparger element with a specific surface area. In the equilateral triangle pattern of FIG. 21, all openings, holes or pores are at equal distances from adjacent openings, holes or pores. Other geometrical patterns such as a simple rectangular grid could also be used, without departing from the broader aspects of the invention. When holes or pores are located at the corners of a rectangular grid, then adjacent holes in the sparger element are located at two different distances, the desired horizontal and vertical distance and the longer distances on the diagonals. Thus, for a specific desired minimum spacing between adjacent holes, the spacing of the holes on the diagonals would be at a distance which is greater than the desired minimum distance. Such a rectangular pattern would result in a smaller number of holes in a sparger element of a specific surface area than would be the case for the more efficient equilateral triangle pattern.

Referring now to FIGS. 11-18, various configurations of the impeller assembly of the bioreactor/bioprocessing system 10 are shown. With specific reference to FIGS. 11-14, in certain embodiments, an impeller assembly 800 includes a hub 810 and at least one blade 812 extending radially from the hub 810. The hub 810 is rotatable about a vertical axis 814 that extends through the center of the hub 810. In some embodiments, the hub 810 may be a magnetic hub configured to be driven by the magnetic drive system or motor (e.g., motor 34 of FIG. 2) positioned exterior to the flexible bag 20 and vessel 12.

Figure 13:
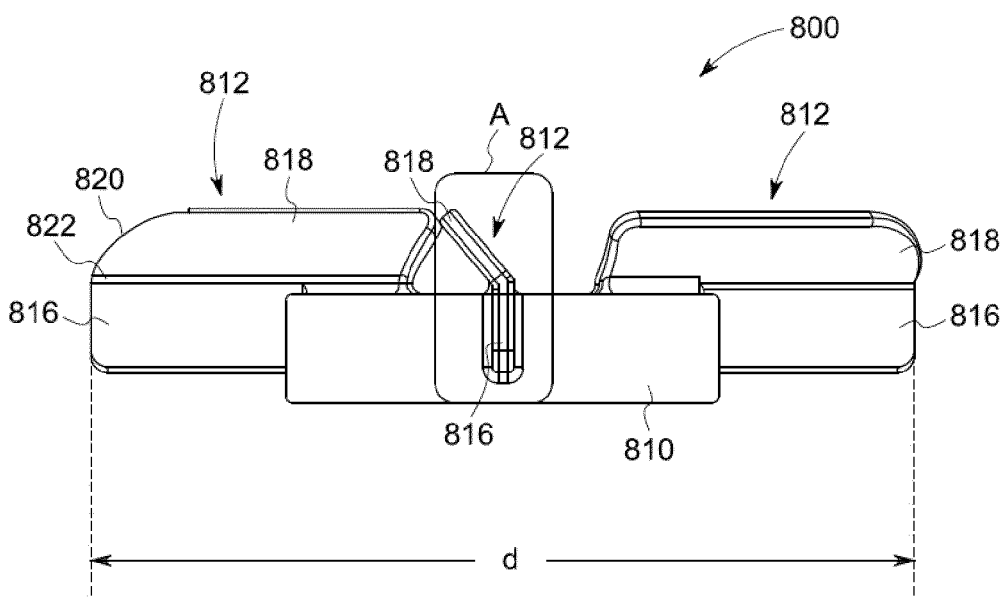
FIG. 13 is a side elevational view of the impeller assembly of FIG. 11.

While the impeller assembly 800 is shown in FIGS. 11-14 as having three blades 812, the impeller assembly 800 may have fewer than three blades (e.g., one blade or two blades) or more than three blades (e.g. four, five or six blades), without departing from the broader aspects of the invention. The blades 812 may be equally spaced from one another about the hub 810. For example, where the impeller assembly 800 has three blades 812, the blades 812 may be spaced 120° apart. The blades 812 each include a first, substantially vertical (e.g. with less than 5°, such as less than 1°, deviation from vertical) portion 816 and a second, non-vertical, non-horizontal, angled portion 818 which extends upwardly from the first portion 816. The first portion 816 and the second portion 818 are shown as being substantially planar (e.g. with a flatness tolerance of less than 5 mm, such as less than 1 mm), although in some embodiments, it is contemplated that one or both of the first and section portions 816, 818 of the blades 812 may have a curved or arcuate shape. As best shown in FIG. 13, the second, angled portion 818 includes a radiused portion 820 at a distal end of the blade 812. A radius 822 is also formed at the intersection between the first, vertical portion 816 and the second, angled portion 818.

Figure 14:
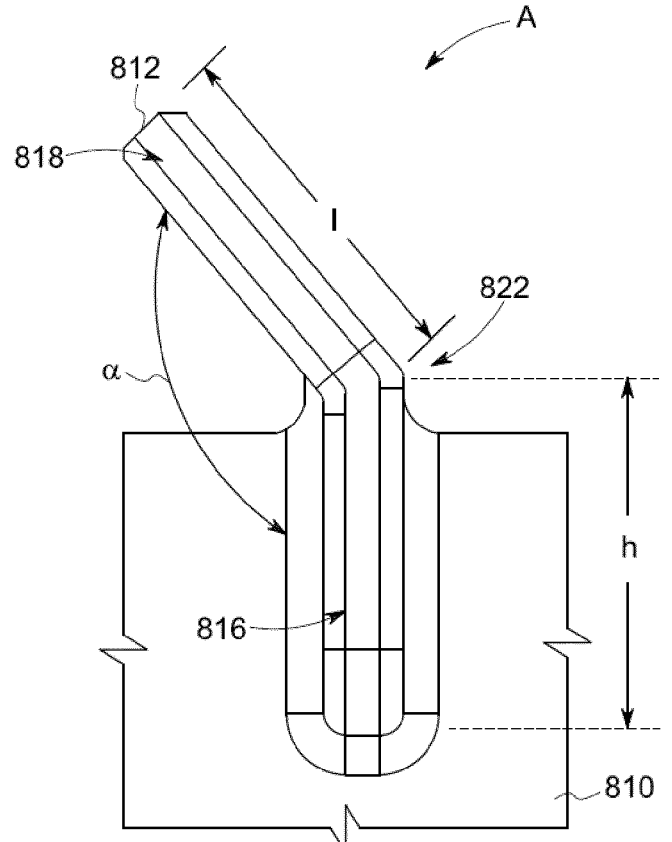
FIG. 14 is an enlarged, detail view of area A of FIG. 13.

With specific reference to FIGS. 13 and 14, the impeller assembly 800 has a diameter, d, defined as the longest linear dimension from blade tip to blade tip. In certain embodiments, the diameter, d, of the impeller may be in a range from about ¼ to about ½ the inner diameter of the vessel 12. As best shown therein, the first, vertical portion 816 and the second, angled portion form an angle, a, therebetween. In some embodiments, the angle, a, is between about 100 degrees to about 180 degrees, such as between 120 and 160 degrees. In certain embodiments, the angle, a is about 135 degrees (e.g. 130-140 degrees), such that the second, angled portion extends at an upward angle of about 45 degrees from horizontal.

As alluded to above, the impeller assembly 800 may be seated on the bottom of the flexible bag 20 in close association with a sparger assembly. For example, the impeller assembly 800 may be connected to a base plate of one of the sparger assemblies disclosed herein, such that the impeller blades 812 are in close association with the gas outlet openings of the sparger assembly. Through testing, it has been shown that the vertically straight portion 816 of the blades 812 of the impeller assembly 800 is particularly efficient in breaking the bubbles input into the flexible bag 20 by the sparger assembly, and delivers high power to the bioreactor system 10. In addition, testing has demonstrated that the angled portion 818 of the blades 812 facilitates mixing of the contents of the flexible bag 20. Accordingly, this combination of straight and angled blade portions yields improved bubble break-up and efficient gas distribution (kLa) with optimum power consumption (i.e., without requiring greater power input or agitation at very high speeds, which can cause shear damage and produce eddies that are harmful to the cells).

In this respect, the impeller assembly 800 optimizes bulk mixing and efficient gas distribution at the gas sparger to provide high oxygen transfer rates and kLa values, which is desirable in intensified cell culture and/or microbial applications. In contrast to existing systems and devices, the impeller assembly 800 achieves this performance while maintaining a relatively low profile (i.e., it remains bottom driven and sits closely to the bottom of the bag 20, allowing for the bag to still be easily collapsed for storage and transport). This simple design also allows for easy user installation and configuration. In particular, in some embodiments, the impeller assembly 800 may be quickly and easily positioned on the mounting shaft of the base plate of a sparger assembly, in the manner hereinbefore described.

Figure 15:
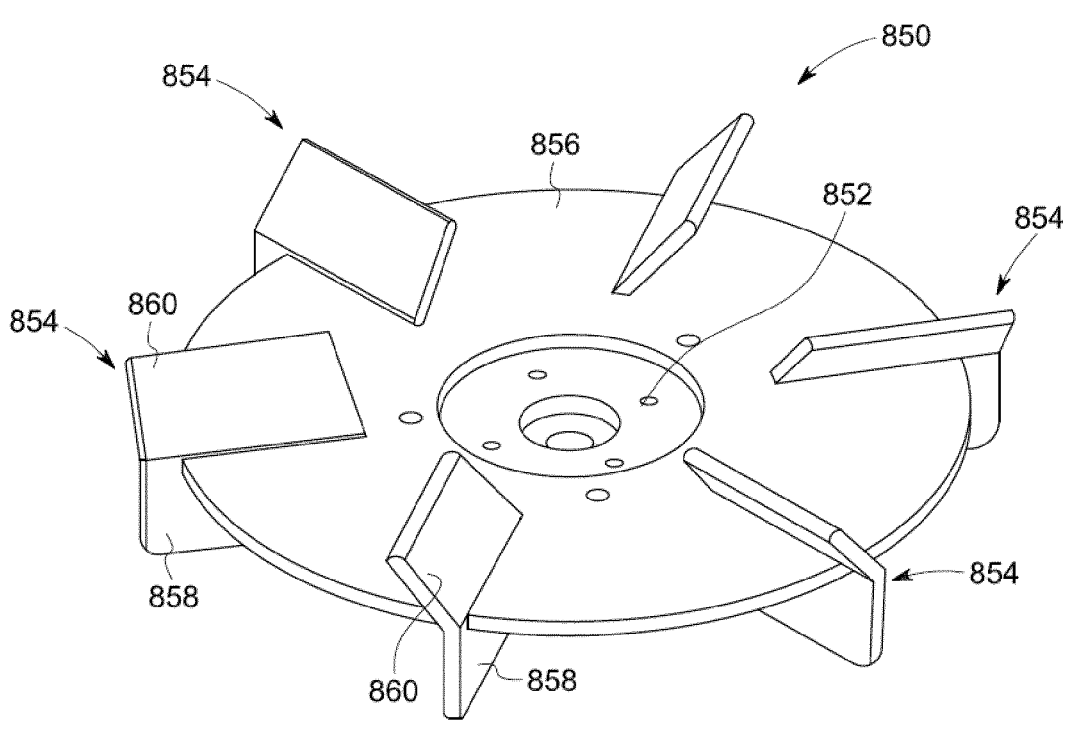
FIG. 15 is a perspective view of an impeller assembly for use with the bioreactor system of FIG. 1, according to certain embodiments of the invention.

Referring now to FIG. 15, an impeller assembly 850 according to certain embodiments of the invention is illustrated. As shown therein, the impeller assembly 850 includes a hub 852 and at least one blade 854 connected to the hub 852. Like the embodiments of FIGS. 11-14, the hub 852 is rotatable about a vertical axis that extends through the center of the hub 852. In some embodiments, the hub 852 may be a magnetic hub configured to be driven by the magnetic drive system or motor (e.g., motor 34 of FIG. 2) positioned exterior to the flexible bag 20 and vessel 12. In certain embodiments, the hub 852 may be formed as (or be otherwise integrated with) a generally flat disc 856 to which the blades 854 extend.

The blades 854 are substantially similar to the blades 812 of the impeller assembly 800 of FIGS. 11-14, and each include a first, substantially vertical (e.g. with less than 5°, such as less than 1°, deviation from vertical) portion 858 and a second, non-vertical, non-horizontal, angled portion 860 which extends upwardly from the first portion 858. The first portion 858 and the second portion 860 are shown as being substantially planar (e.g. with a flatness tolerance of less than 5 mm, such as less than 1 mm), although in some embodiments, it is contemplated that one or both of the first and section portions 858, 860 of the blades 854 may have a curved or arcuate shape. As shown in FIG. 15, in some embodiments, the first, vertical portion 858 extends downwardly from the distribution disc 856, while the second portion 860 extends upwardly at an angle from the distribution disc 856. The blades 854 may terminate at the outer periphery of the distribution disc 856, or may extend beyond such outer periphery to an extent, as shown in FIG. 15.

Figure 16:
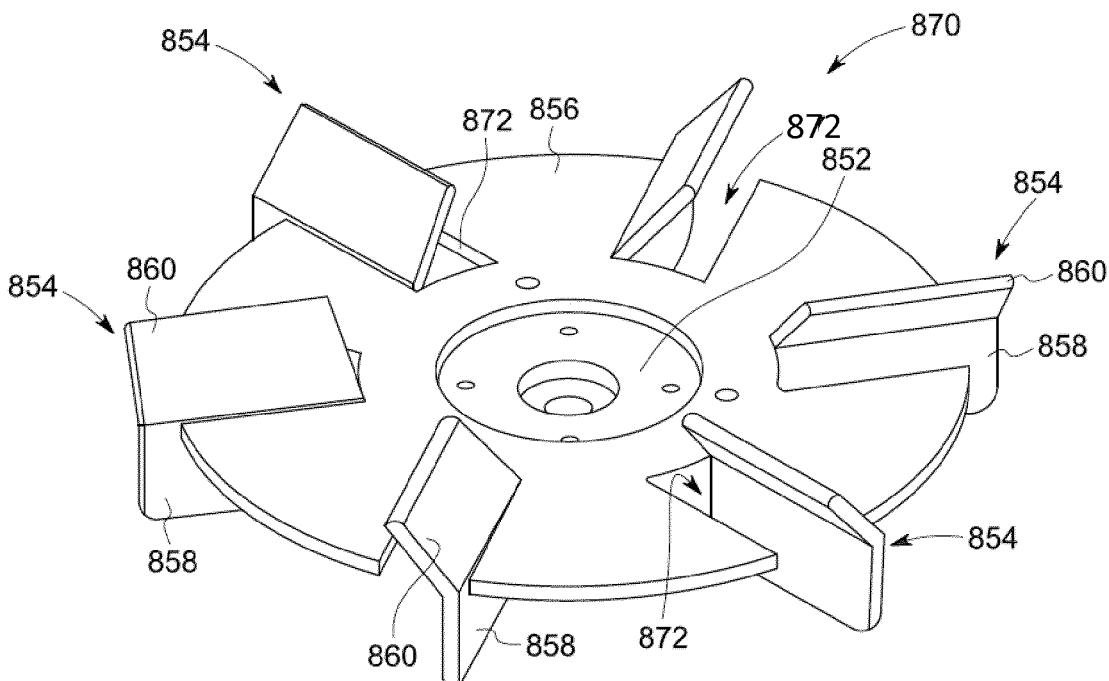
FIG. 16 is a perspective view of an impeller assembly for use with the bioreactor system of FIG. 1, according to certain embodiments of the invention.

Turning now to FIG. 16, another impeller assembly 870 according to some embodiments of the invention is illustrated. The impeller assembly 870 is substantially similar to the impeller assembly 850 of FIG. 15, where like reference numerals designate like parts. As shown in FIG. 16, however, the distribution disc 856 may additional include radial slots 872 adjacent to each (or at least some of) the blades 854.

Figures 25, 26:
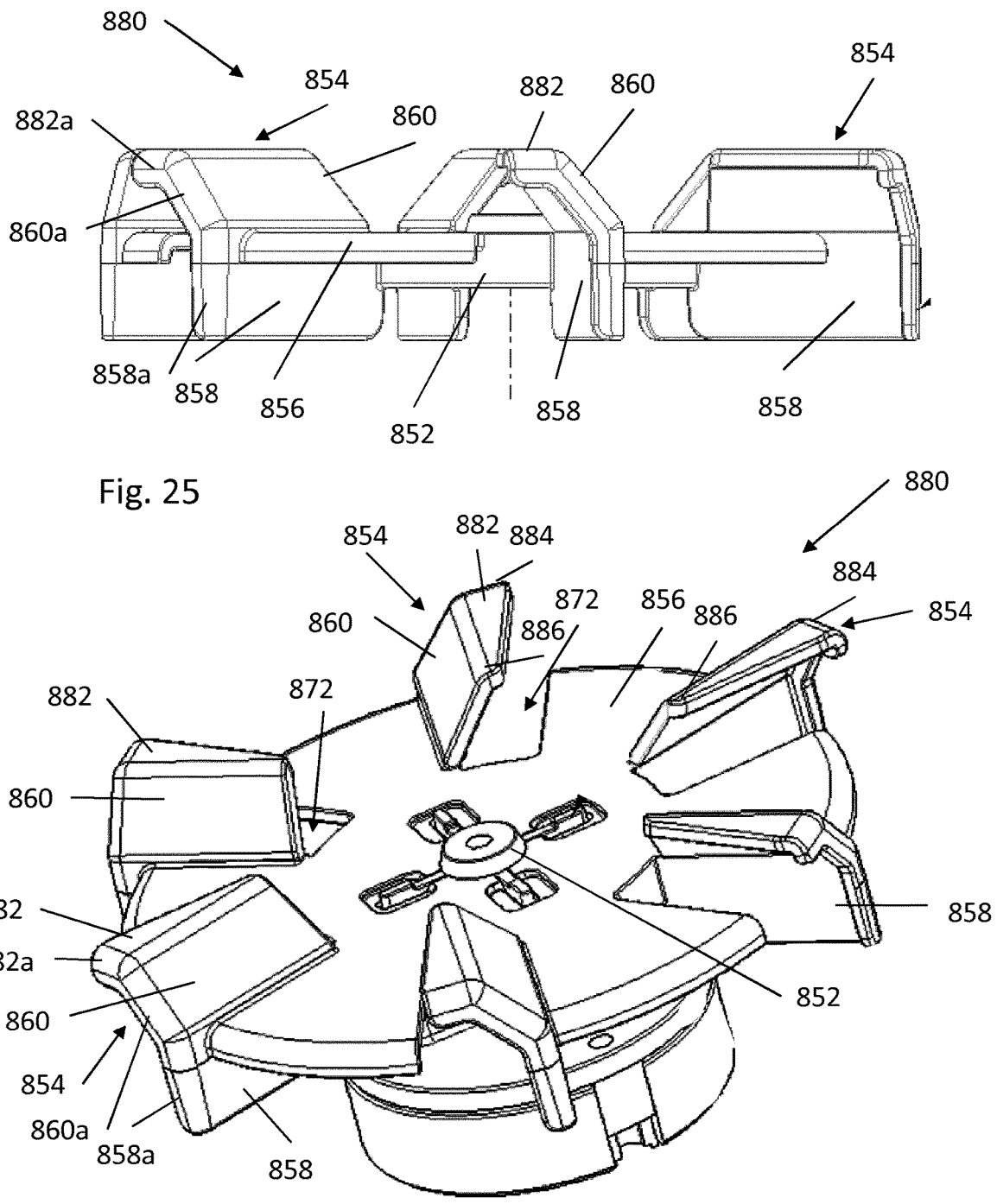
FIG. 25 is a side view an impeller assembly for use with the bioreactor system of FIG. 1, according to certain embodiments of the invention.
FIG. 26 is a perspective view of the impeller assembly of FIG. 25.

FIGS. 25 and 26 show an impeller assembly 880, where each blade 854, in addition to the first substantially vertical portion 858 and the second angled portion 860, further comprises a third substantially horizontal (e.g. with less than 5°, such as less than 1°, deviation from horizontal) portion 882, extending from the top end of the second portion. The third portion may have a distal end 884 which is wider than a proximal end 886. It can even be of substantially triangular shape, with the distal end 884 forming a base of a triangle. The distal edges 858a, 860a and 882a of the first, second and third portions can suitably be radiused in order to avoid potential damage to the walls of the flexible bioprocessing bag.

While the impeller assemblies 850, 870, 880 of FIGS. 15-16 and 25-26 have six blades, the impeller assemblies may have more or fewer than six blades, e.g. 3, 4, 5, 7 or 8 blades, without departing from the broader aspects of the invention. In the embodiments of FIGS. 15 and 16, the vertical blade portions of the blades provide for efficient radial liquid flow, while the angled blade portions allow for axial fluid flow. Moreover, the distribution disc 856 functions to entrap and enrich air/gas bubbles from the sparger assembly before dispersing them. The slots 872 in the distribution disc 856, as shown in FIG. 16, allow for a different bubble distribution pattern. These impeller assembly designs provide for proper mixing and mass transfer of oxygen from the gas phase to the liquid phase, which is essential for cell culture for biopharmaceutical manufacturing, for example, where at very high cell concentrations the demand for oxygen and uniform mixing is very high. In addition, the impeller assemblies shown herein effectively disperse the gas bubbles from the sparger and mix efficiently, without agitating at very high speeds, which can cause shear damage and produce harmful eddies.

Figure 17:
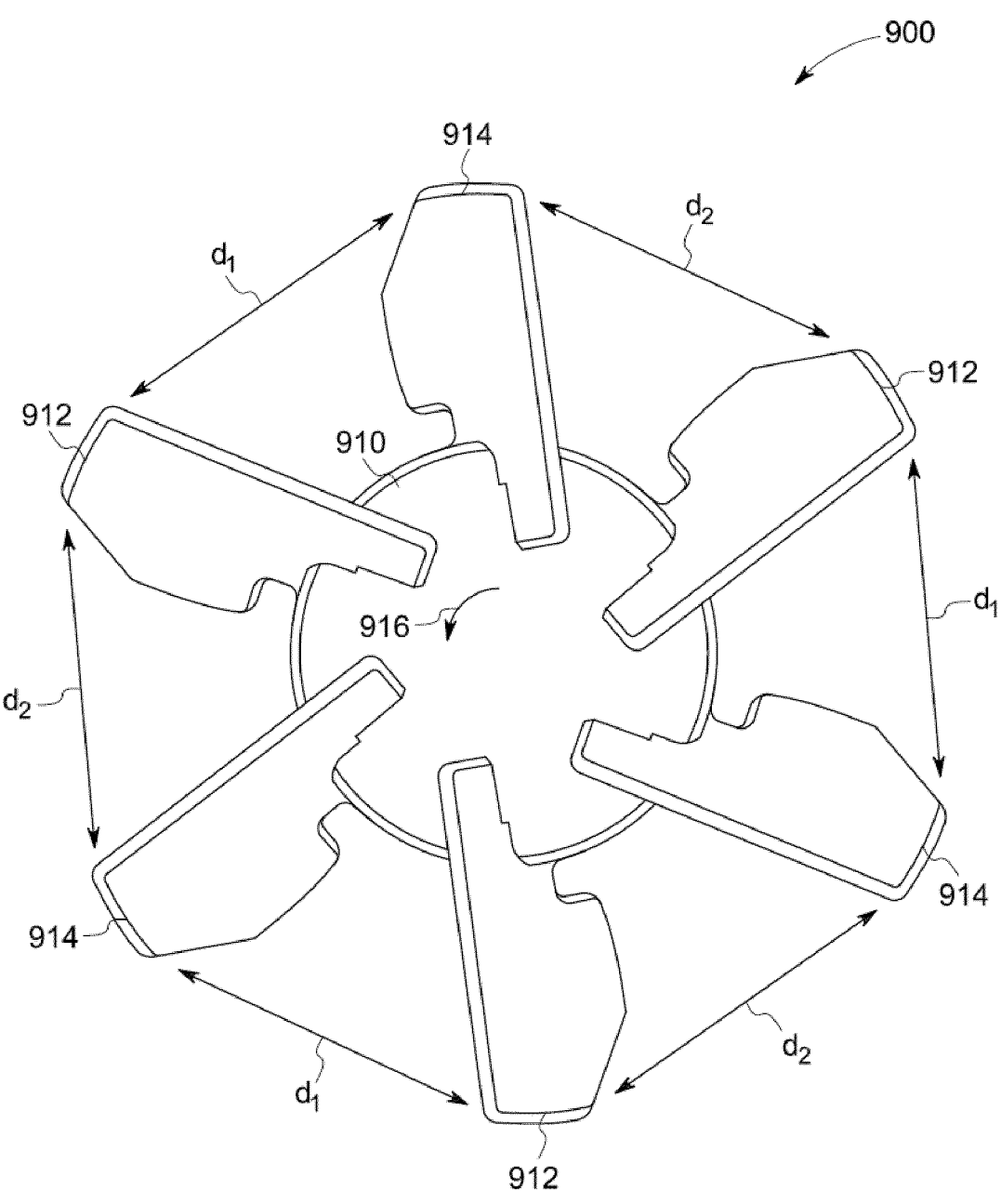
FIG. 17 is a perspective view of an impeller assembly for use with the bioreactor system of FIG. 1, according to certain embodiments of the invention.

Turning now to FIG. 17, an impeller assembly 900 according to some embodiments of the invention is illustrated. The impeller assembly 900 includes a hub 910 and a plurality of blades 912, 914 attached to the hub and extending radially outward from the hub 910. In certain embodiments, the hub 910 is a magnetic hub configured to be driven by an external magnetic drive system or motor, as discussed above. While FIG. 17 illustrates impeller assembly 900 having six blades 912, 914, the impeller assembly may have fewer or more than six blades without departing from the broader aspects of the invention.

In some embodiments, one or more the blades 912, 914 are connected to the hub 910 at angles offset from a radial line extending from the impeller axis. For example, blades 912 may be angled forward of a radial line extending from the impeller axis with respect to a direction of rotation 916 of the impeller assembly 900, while blades 914 may be angled rearward of a radial line extending from the impeller axis with respect to the direction of rotation 916 of the impeller assembly 900. As shown in FIG. 17, the blades may alternate between being forward-angled or rearward-angled. In such an implementation, this blade configuration results in longer and shorter distances between the tips of the blades as compared to uniform distances between the blade tips in the absence of such angled or canted blades. For example, a distance, d1, between the tip of a rearwardly-angled blade 914 and the next adjacent forwardly-angled blade 912 (moving in the direction of rotation of the impeller assembly 900) is increased as compared to the distance between blade tips if the blades were oriented along a radial line extending from the center of the hub 910. In addition, a distance, d2, between the tip of a forwardly-angled blade 912 and the next adjacent rearwardly-angled blade 914 (moving in the direction of rotation of the impeller assembly 900) is decreased as compared to a distance between blade tips if the blades were oriented along a radial line extending from the center of the hub 910. In this respect, the impeller assembly 900 has alternating longer and shorter distances between the tips of the blades.

Figure 18:
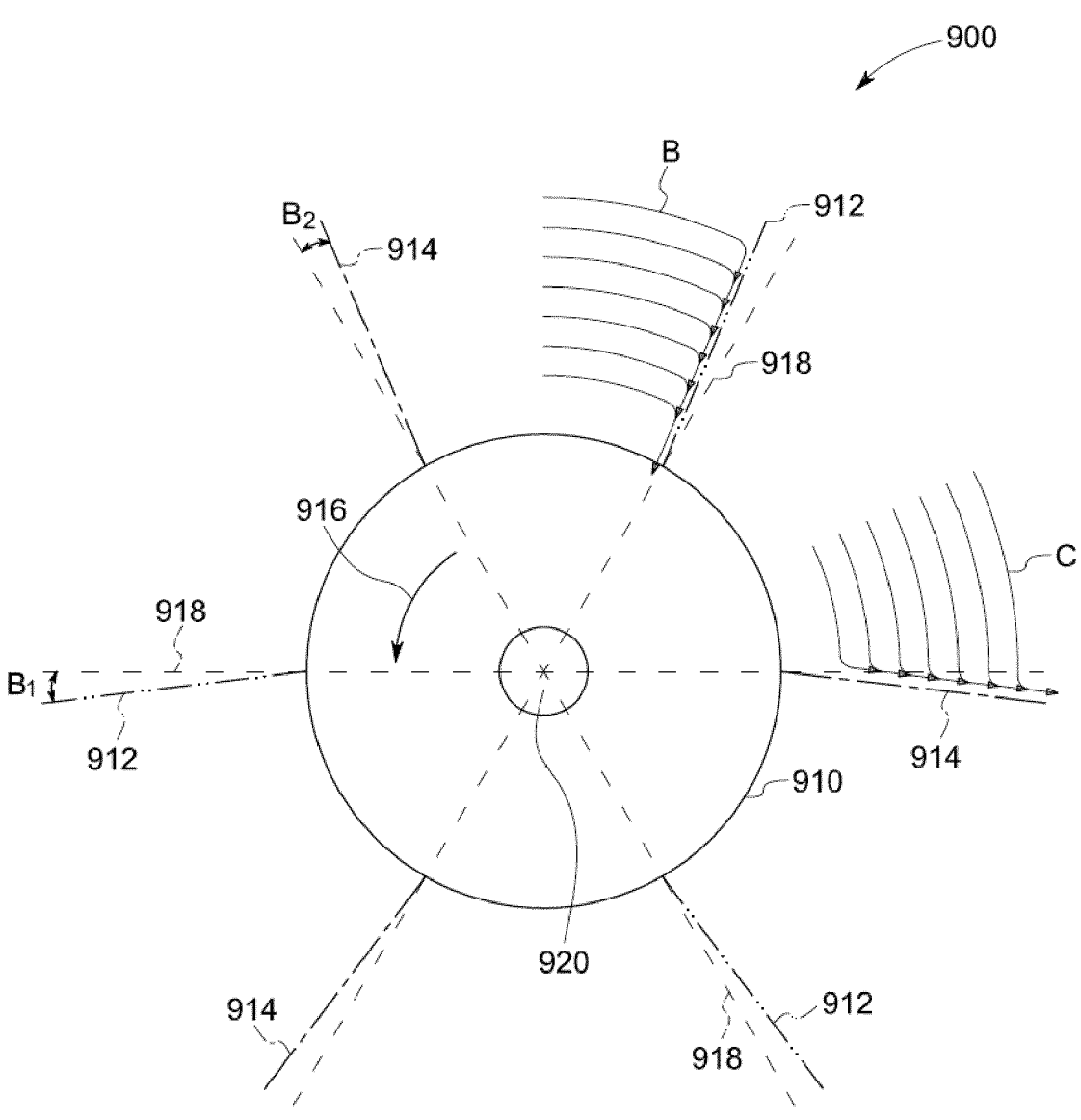
FIG. 18 is a schematic illustration of the impeller assembly of FIG. 17.

This canted configuration of the blades 912, 914 of the impeller assembly is more clearly shown in FIG. 18. As illustrated therein, alternating blades 912 are oriented at a leading angle, β1, with respect to true radial lines 918 extending from the central axis 920 of the impeller assembly 900. In contrast, alternating blades 914 are oriented at a lagging angle, β2, with respect to true radial lines 918 extending from the central axis 920 of the impeller assembly 900. In certain embodiments, the leading angle β1 of the blades 912 may be equivalent to the lagging angle, β2, of the blades 914. For example, in some embodiments, leading angle β1 and lagging angle β2 may be between about 5 degrees and about 30 degrees. In some embodiments, leading angle β1 and lagging angle β2 may be between about 5 degrees and about 10 degrees. In certain embodiments, leading angle β1 and lagging angle β2 may be about 7 degrees, such as 6-8 degrees. In other embodiments, the leading angle, β1, of the blades 912 may be different from the lagging angle, β2, of the blades 914. In yet other embodiments, one or more of the blades 912 may have a different leading angle, β1, than at least another of the blades 912. Similarly, one or more of the blades 914 may have a different lagging angle, β2, than at least another of the blades 914. It is contemplated that the number of blades with leading angles may be the same or different than the number of blades with lagging angles.

In operation, the blades 912 oriented at leading angles with respect to a true radial line 918 extending from the central axis 920 function to pull liquid inwardly towards the hub 910, in the direction of arrows B, as shown in FIG. 18. Conversely, the blades 914 oriented at lagging angles with respect to a true radial line 918 extending from the central axis 920 function to push liquid away from the hub 910, in the direction of arrows C, as shown in FIG. 18. Accordingly, the impeller assembly 900 can be utilized to increase mixing effectiveness, which can improve oxygen transfer within the bioreactor system 10. It is contemplated that the blade orientation/canting aspects of the invention may be employed in conjunction with existing blade geometries/shapes/configurations known in the art to improve impeller mixing capability.

Figure 19:
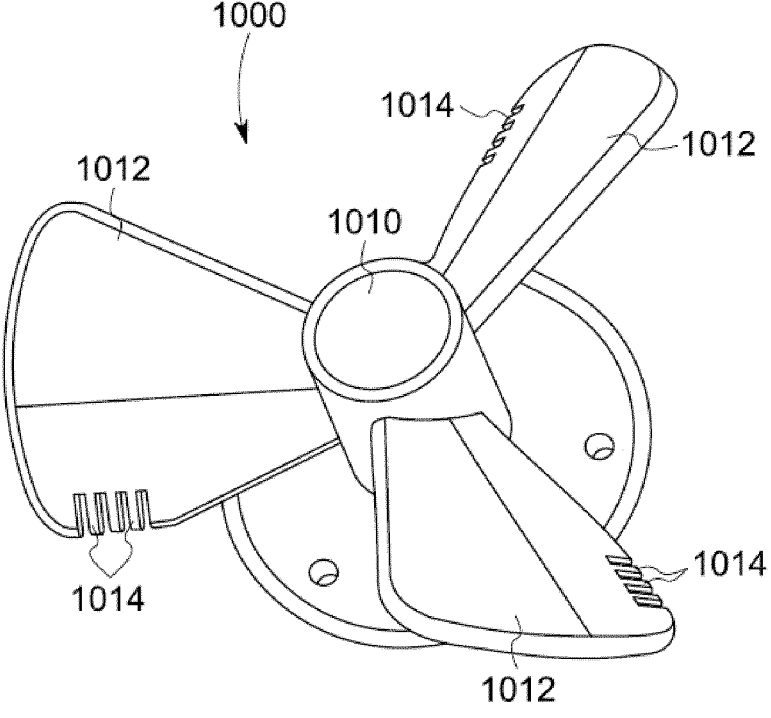
FIG. 19 is a perspective view of an impeller assembly for use with the bioreactor system of FIG. 1, according to certain embodiments of the invention.

With reference to FIG. 19, an impeller assembly according to some embodiments of the invention is illustrated. The impeller assembly 1000 includes a hub 1010 and a plurality of blades 1012 mounted to the hub 1010. While the impeller assembly 1000 of FIG. 19 has three blades 1012, fewer or more than three blades may be employed without departing from the broader aspects of the invention. In certain embodiments, the impeller assembly 1000 is a marine-type impeller having arcuate or curved blades 1012. As illustrated in FIG. 19, in some embodiments, one or more of the blades 1012 includes a plurality of slots 1014. In certain embodiments, the slots 1014 are generally vertically-extending slots and are positioned at a location on the blades 1012 that is generally aligned with, in a vertical direction, the location on a sparger assembly where the sparge gas is released into the flexible bag 20. In some embodiments, the slots 1014 are formed on a forward or leading edge of the blades 1012.

In use, the impeller assembly 1000 may be mounted to the mounting shaft of a sparger assembly, as discussed above. As indicated above, the slots 1014 are positioned so that when the blades 1012 rotate, the slots 1014 pass closely over the gas outlet openings in the sparger assembly.

Figure 20:
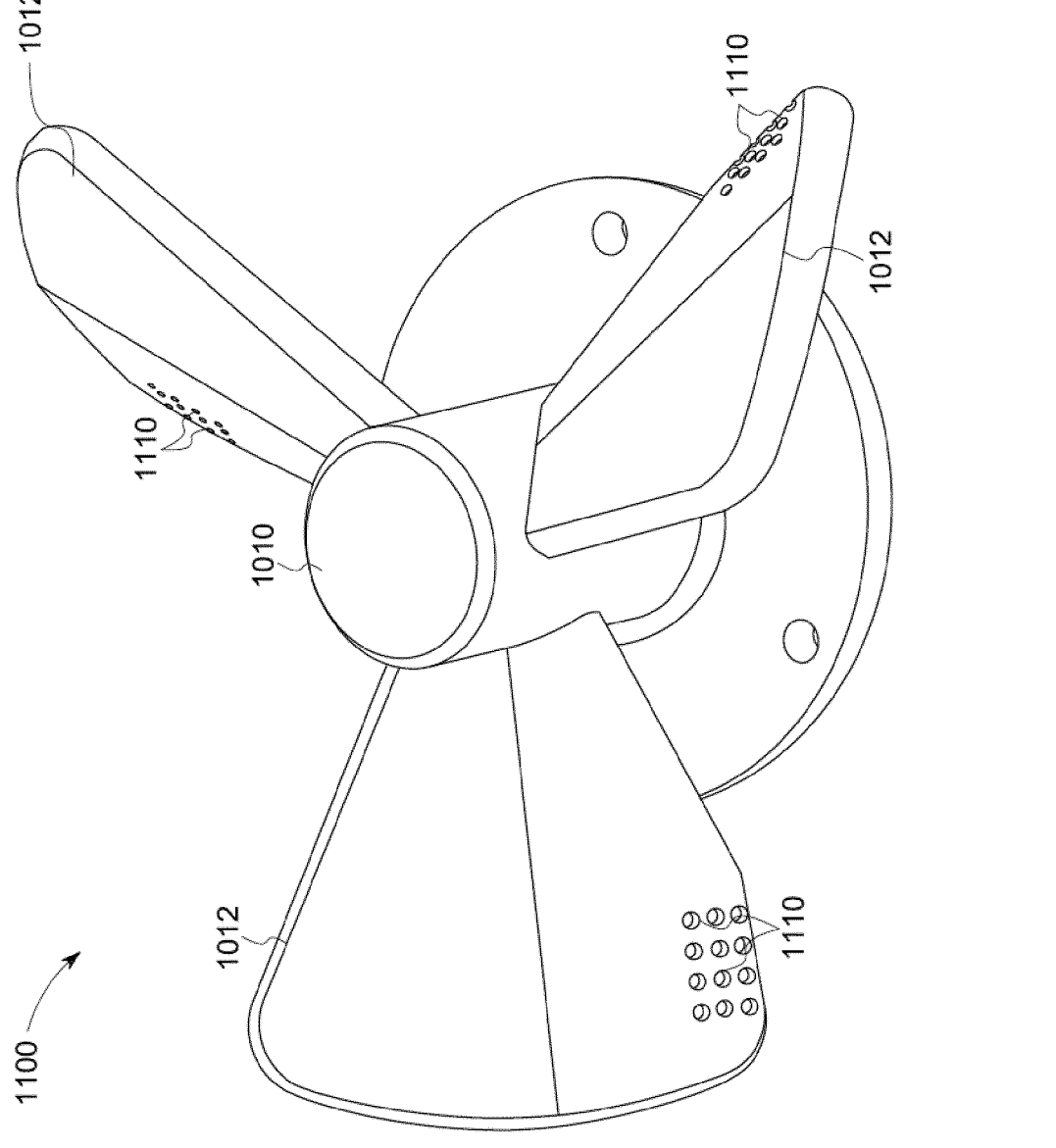
FIG. 20 is a perspective view of an impeller assembly for use with the bioreactor system of FIG. 1, according to certain embodiments of the invention.

Referring finally to FIG. 20, a similar impeller assembly 1100 is illustrated. Rather than having slots in the forward edge of the blades 1012, however, an array of depressions, holes or apertures 1110 may be formed in a leading edge of the blades 1012. Similar to the embodiments of FIG. 19, the apertures 1110 are disposed at a location that generally corresponds to the location of the gas outlet openings of the sparger assembly on which the impeller assembly 1100 is disposed.

It is contemplated that slots or apertures may be integrated with any existing impeller designs or configurations for a bioreactor system, as well as the impeller assembly configurations described herein. By utilizing an impeller with slots or apertures in the area of the blade that passes closely over the gas outlet openings of the sparger assembly, the interfacial contact between the blades of the impeller and the fluid within the flexible bag 20 may be increased. Accordingly, the impeller assemblies 1000, 1100 provide for more efficient gas distribution at the gas sparger to provide high oxygen transfer rates and kLa values desired for enhanced cell culturing, without increasing the power requirements on the impeller drive system.

Embodiments of the impeller assemblies and sparger assemblies disclosed herein and their combinations provide various means of increasing kLa of a bioreactor system (i.e., achieving more efficient gas distribution) to support intensified cell culture and/or microbial applications. It is contemplated that the impeller assemblies disclosed herein may be utilized in conjunction with any existing sparger assembly. Similarly, the sparger assemblies disclosed herein may be utilized in connection with a number of existing impeller assemblies. Still further, it is envisioned that any of the impeller assemblies disclosed herein may be utilized in conjunction with any of the sparger assemblies also disclosed herein, to provide both improved bulk mixing and efficient gas dispersion. In this respect, the configuration of both the impeller assemblies and sparger assemblies of the invention facilitates simple user manipulation or configuration of a combined impeller and sparger assembly. In particular, the impeller and/or sparger assemblies of the invention can be easily manipulated (e.g., by interchanging the aeration manifolds on the sparger and/or connecting different impellers to the sparger base plate) to achieve almost any level of bulk mixing or gas dispersion desired, depending on the particular cell culturing or bioprocessing operations being carried out within the bioprocessing system 10.

In some embodiments, a sparger assembly for a bioprocessing system includes a base plate and at least one aeration manifold removably connected to the base plate, each aeration manifold including at least one inlet for receiving a gas and a plurality of gas outlet openings for delivering the gas to a fluid within the bioprocessing system. In certain embodiments, the at least one aeration manifold is in spaced vertical relation to the base plate when connected to the base plate. In some embodiments, the at least one aeration manifold may be annular in shape. In certain embodiments, the at least one aeration manifold is two aeration manifolds including a first aeration manifold and a second aeration manifold, the aeration manifolds being arranged in the shape of a semi-circular arc. In some embodiments, the at least one aeration manifold is four aeration manifolds, the aeration manifolds forming a quarter-circular arc. In certain embodiments, a size of the gas outlet openings of at least one of the aeration manifolds is different from a size of the gas outlet openings of at least another of the aeration manifolds. In some embodiments, the aeration manifolds are arranged on the base plate such that the size of the gas outlet openings of each aeration manifold is different from the size of the gas outlet openings of an immediately adjacent aeration manifold. In certain embodiments, a first pair of the aeration manifolds are arranged on the base plate to form a first semi-circle, and a second pair of the aeration manifolds are arranged on the base plate to form a second semi-circle. The gas outlet openings of the first pair of aeration manifolds are a first size, and gas outlet openings of the second pair of aeration manifolds are a second size that is different from the first size. In some embodiments, the at least one aeration manifold is at least two aeration manifolds including a first aeration manifold and a second aeration manifold concentrically mounted with the first aeration manifold, wherein at least one of the first aeration manifold and the second aeration manifold has a pleated or sprocket-like periphery. In some embodiments, the at least one aeration manifold is a plurality of aeration manifolds, at least one of the aeration manifolds is raised above the base plate a first distance, and at least another of the aeration manifolds is raised above the base plate at a second distance, wherein the first distance is greater than the second distance. In certain embodiments, the base plate includes a shaft for receiving an impeller assembly and positioning the impeller assembly so that blades of the impeller assembly are located a distance above the at least one aeration manifold. In some embodiments, the base plate includes an aperture for interfacing with a drain port in a flexible bioprocessing bag and a drain port of a support vessel that receives the flexible bioprocessing bag.

In certain embodiments, a bioprocessing system, includes a vessel, a flexible bioprocessing bag positionable within the vessel, and a sparger assembly positioned at a bottom of the flexible bioprocessing bag, the sparger assembly including a base plate and at least one aeration manifold removably coupled to, and supported by, the base plate. Each aeration manifold includes at least one inlet for receiving a gas and at least one gas outlet opening for delivering the gas to a fluid within the flexible bioprocess bag. In some embodiments, the at least one aeration manifold is in spaced vertical relation to the base plate when connected to the base plate. In certain embodiments, the at least one aeration manifold is annular in shape. In some embodiments, the at least one aeration manifold is two aeration manifolds including a first aeration manifold and a second aeration manifold, each of the aeration manifolds being arranged a semi-circular arc in shape. In certain embodiments, the at least one aeration manifold is four aeration manifolds, each of the aeration manifolds being an approximately quarter-circular arc in shape. In some embodiments, a size of the at least one gas outlet opening of at least one of the aeration manifolds is different from a size of the at least one gas outlet opening of at least another of the aeration manifolds. In certain embodiments, the base plate includes an aperture for interfacing with a drain port in the flexible bioprocessing bag and a drain port of the vessel.

In some embodiments, a sparger assembly for a bioprocessing system includes a base plate, at least one aeration manifold removable connected to the base plate and supported in raised position with respect to the base plate, each aeration manifold including at least one inlet for receiving a gas and at least one gas outlet opening for delivering the gas to a fluid within the bioprocessing system, and a mounting device enabling coupling of an impeller of the bioprocessing system to the sparger assembly in close association with the aeration manifold.

In some embodiments, an impeller assembly for a bioprocessing system includes a hub and at least one blade operatively connected to the hub. The at least one blade includes a first portion connected to the hub and extending generally vertically, and a second portion extending at an upward angle from the first portion. In certain embodiments, the first portion and second portion are substantially planar (e.g. with a flatness tolerance of less than 5 mm, such as less than 1 mm). In some embodiments, the at least one blade is three blades.

In certain embodiments, the second portion includes a radiused distal end. In some embodiments, the hub includes a generally planar disc, and the disc includes at least one slot adjacent to each of the at least one blade. In some embodiments, the first portion and the second portion form an angle between about 100 degrees and about 180 degrees therebetween. In certain embodiments, the hub is a magnetic hub.

In certain embodiments, an impeller assembly for a bioprocessing system includes a hub having a central axis and a plurality of blades extending from the hub, at least one of the blades being oriented at one of a leading angle or a lagging angle with respect to a radial line extending from the central axis of the hub. In some embodiments, at least one of the plurality of blades is oriented at a leading angle with respect to a first radial line extending from the central axis, and at least another of the plurality of blades is oriented at a lagging angle with respect to a second radial line extending from the central axis. In certain embodiments, each of the plurality of blades is oriented at one of a leading angle or a lagging angle with respect to a respective radial line extending from the central axis of the hub, and define leading or lagging blades of the plurality of blades. In some embodiments, the leading and lagging blades are alternately positioned in a direction of rotation of the hub. In certain embodiments, the leading angle is between about 5 degrees and about 30 degrees and the lagging angle is between about 5 degrees and about 30 degrees. In some embodiments, with respect to a direction of rotation of the impeller assembly, a distance between a tip of leading blade and a next-adjacent lagging blade is less than a distance between a tip of a lagging blade and a next-adjacent leading blade. In certain embodiments, the impeller assembly has a largest diameter of between about ¼ to about V2 times the diameter of a bioreactor vessel within which the impeller assembly is configured to be positioned In some embodiments, an impeller assembly for a bioprocessing system includes a hub and a plurality of blades extending from the hub, the blades each having a leading edge and a trailing edge. At least one of the blades includes an array of slots or apertures in a leading edge of the blade. In some embodiments, the blades are marine-type blades. In certain embodiments, the slots are generally vertically-extending slots. In some embodiments, each of the blades of the plurality of blades includes an array of slots or apertures in the leading edge of the blade, respectively. In certain embodiments, the array of slots or apertures is located at a radial position on the blades that corresponds to a gas outlet of a sparger assembly of the bioprocessing system.

As used herein, an element or step recited in the singular and proceeded with the word "a" or "an" should be understood as not excluding plural of said elements or steps, unless such exclusion is explicitly stated. Furthermore, references to "embodiments" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. Any directional terms, such as "top", "bottom", "upper", "lower", "above", "below", "horizontal", "vertical" etc. refer to the directions as shown in the drawings, which are also the directions in the operational position of the bioprocessing system.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A sparger assembly for a bioprocessing system, comprising:
   a base plate; and
   at least one aeration manifold removably connected to the base plate, each aeration manifold including at least one inlet for receiving a gas and a plurality of gas outlet openings for delivering the gas to a fluid within the bioprocessing system; and
   an impeller assembly comprising a hub and at least one blade operatively connected to the hub, the at least one blade including a first portion connected to the hub and extending generally vertically, a second portion extending at an upward angle from the first portion, and a third portion extending from the second portion, wherein the third portion is substantially horizontal, wherein the third portion has a distal end and a proximal end, with the distal end being wider than the proximal end,
   wherein the base plate includes a mounting device enabling coupling of the impeller assembly to the base plate adjacent to the at least one aeration manifold; and
   wherein the at least one aeration manifold is arcuate in shape.

2. The sparger assembly of claim 1, wherein the at least one aeration manifold is in spaced vertical relation to the base plate when connected to the base plate.

3. The sparger assembly of claim 1, wherein the at least one aeration manifold is annular in shape.

4. The sparger assembly of claim 1, wherein said at least one aeration manifold comprises:
   an inlet chamber unit with an inlet chamber fluidically connected to a tube connector;
   a porous plate sealed to said inlet chamber unit by a gasket; and
   a frame fastened to said inlet chamber unit and engaging said porous plate to keep the plate and the gasket in sealing abutment with the inlet chamber unit.

5. The sparger assembly of claim 4, wherein said frame is fastened to said inlet chamber unit by a plurality of snap joints.

6. The sparger assembly of claim 4, wherein said inlet chamber unit comprises a plurality of feet, fastened to posts in said base plate by snap joints.

7. The sparger assembly of claim 1, wherein the at least one aeration manifold is two aeration manifolds including a first aeration manifold and a second aeration manifold, the aeration manifolds being arranged in a circular configuration on the base plate.

8. The sparger assembly of claim 1, wherein the at least one aeration manifold is four aeration manifolds, the aeration manifolds being arranged in a circular configuration on the base plate.

9. The sparger assembly of claim 8, wherein a size of the gas outlet openings of at least one of the aeration manifolds

21 is different from a size of the gas outlet openings of at least another of the aeration manifolds.

10. The sparger assembly of claim 7, wherein the aeration manifolds are arranged on the base plate such that the size of the gas outlet openings of each aeration manifold is different from the size of the gas outlet openings of an immediately adjacent aeration manifold.

11. The sparger assembly of claim 8, wherein:

a first pair of the aeration manifolds are arranged on the base plate to form a first semi-circle; and a second pair of the aeration manifolds are arranged on the base plate to form a second semi-circle;

wherein the gas outlet openings of the first pair of aeration manifolds are a first size; and wherein the gas outlet openings of the second pair of aeration manifolds are a second size that is different from the first size.

12. The sparger assembly of claim 1, wherein:

the at least one aeration manifold is at least two aeration manifolds including a first aeration manifold and a second aeration manifold concentrically mounted with the first aeration manifold;

wherein at least one of the first aeration manifold and the second aeration manifold has a pleated periphery.

13. The sparger assembly of claim 1, wherein:

the at least one aeration manifold is a plurality of aeration manifolds; and wherein at least one of the aeration manifolds is raised above the base plate a first distance;

wherein at least another of the aeration manifolds is raised above the base plate at a second distance; and wherein the first distance is greater than the second distance.

14. The sparger assembly of claim 1, wherein the base plate includes a shaft for receiving the impeller assembly and positioning the impeller assembly so that blades of the impeller assembly are located a distance above the at least one aeration manifold.

15. The sparger assembly of claim 1, wherein the base plate includes an aperture for interfacing with a drain port in a flexible bioprocessing bag and a drain port of a support vessel that receives the flexible bioprocessing bag.

16. The sparger assembly of claim 1, wherein the third portion is substantially triangular in shape.

17. The sparger assembly of claim 4, wherein the frame comprises one or more ribs extending between opposing sides of the fame.

* * * * *